(12) United States Patent
Kim et al.

(10) Patent No.: US 11,833,204 B2
(45) Date of Patent: Dec. 5, 2023

(54) VISIBLE LIGHT-ACTIVATABLE NANOPARTICLES FOR CANCER IMMUNOTHERAPY AND USE THEREOF

(71) Applicant: KOREA INSTITUTE OF SCIENCE AND TECHNOLOGY, Seoul (KR)

(72) Inventors: Kwangmeyung Kim, Seoul (KR); In-Cheol Sun, Seoul (KR); Man Kyu Shim, Seoul (KR); Ji Woong Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 17/529,450

(22) Filed: Nov. 18, 2021

(65) Prior Publication Data

US 2022/0370611 A1 Nov. 24, 2022

(30) Foreign Application Priority Data

May 6, 2021 (KR) .................. 10-2021-0058445

(51) Int. Cl.
*A61K 31/351* (2006.01)
*A61K 41/00* (2020.01)
*A61P 35/00* (2006.01)
*A61K 47/69* (2017.01)

(52) U.S. Cl.
CPC ........ *A61K 41/0076* (2013.01); *A61K 31/351* (2013.01); *A61K 47/6929* (2017.08); *A61P 35/00* (2018.01)

(58) Field of Classification Search
CPC .................................................... A61K 31/351
USPC ........................................................ 514/460
See application file for complete search history.

(56) References Cited

FOREIGN PATENT DOCUMENTS

| KR | 1020140048008 A | 4/2014 |
| KR | 1020190126431 A | 11/2019 |
| KR | 1020210032160 A | 3/2021 |

*Primary Examiner* — Taofiq A Solola
(74) *Attorney, Agent, or Firm* — Rabin & Berdo, P.C.

(57) ABSTRACT

Disclosed are visible light-activatable antitumor self-assembled nanoparticles or antitumor immunity-inducing self-assembled nanoparticles. The self-assembled nanoparticles induce potent apoptosis in cancer cells and increase their own anticancer immunogenicity, thereby maximizing their therapeutic efficacy for cancer.

7 Claims, 24 Drawing Sheets

Specification includes a Sequence Listing.

FIG. 2

-7 day
1st tumor inoculation 0, 2 day
Treatment 3 day
2nd tumor inoculation 20 day
2nd tumor analysis

VISIBLE LIGHT-ACTIVATABLE NANOPARTICLES FOR CANCER IMMUNOTHERAPY AND USE THEREOF

BACKGROUND OF THE INVENTION

1. Field of the Invention

The present invention relates to visible light-activatable self-assembled nanoparticles for cancer immunotherapy.

2. Description of the Related Art

In recent years, cancer immunotherapy has received attention as the most promising therapeutic approach for cancer treatment. Immuno-oncology drugs can be classified into immune checkpoint inhibitors, immune cell therapeutics, anticancer vaccines, and viral immunotherapeutics.

Particularly, immune checkpoint inhibitors act to block the interaction between major immune checkpoint molecules with the ability to suppress T cell activity and function, such as PD-1/PD-L1, and their receptors/ligands. It was reported that immune checkpoint inhibitors exhibit superior and sustained therapeutic effects in some patients and carcinomas but still suffer from limitations such as poor therapeutic effects and resistance in a significant number of patients depending on their cancer immunogenicity and microenvironment.

Patients with a low response rate to immune checkpoint inhibitors were reported to innately have small numbers of immune cells and tumor-infiltrating lymphocytes. As a solution to the above problems, there is an urgent need to develop a therapeutic approach for maximizing the efficiency of cancer immunotherapy using an immune checkpoint inhibitor by increasing its own anticancer immunogenicity.

PRIOR ART DOCUMENTS

Patent Documents

Patent Document 1. Korean Patent Publication No. 10-2019-0126431

SUMMARY OF THE INVENTION

The present invention has been made in an effort to solve the above-described problems and one object of the present invention is to provide self-assembled nanoparticles including complexes in which a hydrophobic anticancer drug and a photosensitizer are bonded to one end and the other end of a central amphipathic peptide represented by Formula 1, respectively.

A further object of the present invention is to provide a pharmaceutical composition for preventing or treating cancer including the self-assembled nanoparticles as active ingredients.

One aspect of the present invention provides self-assembled nanoparticles including complexes in which a hydrophobic anticancer drug and a photosensitizer are bonded to one end and the other end of a central amphipathic peptide represented by Formula 1, respectively:

Xaa1-Arg-Arg-Gly (1)   (SEQ ID NO: 2)

wherein Xaa is selected from alanine, valine, isoleucine, leucine, methionine, phenylalanine, tyrosine, and tryptophan.

The self-assembled nanoparticles may have an average diameter of 50 to 500 nm.

The hydrophobic anticancer drug may be selected from the group consisting of doxorubicin, cyclophosphamide, mechlorethamine, uramustine, melphalan, chlorambucil, ifosfamide, bendamustine, carmustine, lomustine, streptozocin, busulfan, dacarbazine, temozolomide, thiotepa, altretamine, duocarmycin, cisplatin, carboplatin, nedaplatin, oxaliplatin, satraplatin, triplatin tetranitrate, 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, camptothecin, topotecan, irinotecan, etoposide, teniposide, mitoxantrone, paclitaxel, docetaxel, ixabepilone, vinblastine, vincristine, vindesine, vinorelbine, estramustine, maytansine, mertansine (DM1), DM4, dolastatin, auristatin E, auristatin F, monomethyl auristatin E, monomethyl auristatin F, derivatives thereof, and combinations thereof.

The cancer may be selected from the group consisting of brain tumor, benign astrocytoma, malignant astrocytoma, pituitary adenoma, meningioma, central nervous system lymphoma, oligodendroglioma, craniopharyngioma, ependymoma, brain stem tumor, head and neck tumor, laryngeal cancer, oropharyngeal cancer, nasal cavity/paranasal sinus cancer, nasopharyngeal cancer, salivary gland cancer, hypopharyngeal cancer, thyroid cancer, oral cavity cancer, chest tumor, small cell lung cancer, non-small cell lung cancer, thymus cancer, mediastinal tumor, esophageal cancer, breast cancer, male breast cancer, abdominal tumor, stomach cancer, liver cancer, gall bladder cancer, biliary tract cancer, pancreatic cancer, small intestine cancer, large intestine cancer, anal cancer, bladder cancer, kidney cancer, prostate cancer, testicular cancer, uterine cancer, cervical cancer, endometrial cancer, ovarian cancer, uterine sarcoma, squamous cell carcinoma, skin cancer, and combinations thereof.

The self-assembled nanoparticles of the present invention are prodrugs that have cancer cell-specific anticancer activity when activated by visible light, are degraded by cathepsin B specifically expressed in tumor tissues, and release the hydrophobic anticancer drug (e.g., doxorubicin) and the photosensitizer (e.g., verteporfin). The self-assembled nanoparticles of the present invention specifically respond to and are activated in tumor cells. Therefore, the use of the self-assembled nanoparticles can avoid serious side effects such as cell damage and death encountered during cancer prevention or treatment.

In addition, the self-assembled nanoparticles of the present invention have an outstanding ability to kill cancer cells and release the photosensitizer to induce potent immunogenic cell death (ICD) in cancer cells during cancer immunotherapy, thereby activating the body's immune system. This immunogenicity improves the infiltration of immune cells into tumor tissues and the activity of immune cells to enable the conversion of cold tumors into hot tumors, leading to a significant enhancement in the efficacy of cancer immunotherapy.

The self-assembled nanoparticles of the present invention can inhibit the growth and proliferation of cancer cells and are highly effective in activating the body's immune system even when used alone. Furthermore, combined administration of the self-assembled nanoparticles according to the present invention and a conventional anticancer drug has a better pharmacological inhibitory effect on cancer recurrence, metastasis, and progression. Therefore, the self-assembled nanoparticles of the present invention are suitable for use in a pharmaceutical composition or combined preparation for preventing or treating cancer.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 2 schematically shows a synthetic procedure for the preparation of visible light-activatable self-assembled nanoparticles;

FIG. 3A shows the size of the self-assembled nanoparticles (LT-NPs) measured by dynamic light scattering (DLS), FIG. 3B shows transmission electron microscopy images revealing the morphologies of the self-assembled nanoparticles (LT-NPs), doxorubicin, and verteporfin (VPF), FIG. 3C shows time-dependent changes in the size of the self-assembled nanoparticles (LT-NPs) in mouse plasma, FIG. 3D shows UV spectra of the self-assembled nanoparticles (LT-NPs), doxorubicin (DOX), verteporfin (VPF), and a mixture of doxorubicin (DOX) and verteporfin (VPF), FIG. 3E shows the fluorescence intensities of the self-assembled nanoparticles (LT-NPs), doxorubicin (DOX), verteporfin (VPF), and a mixture of doxorubicin (DOX) and verteporfin (VPF), FIG. 3F shows cleavages of the self-assembled nanoparticles (LT-NPs) after enzymatic reaction with cathepsin B for different times (0, 9, and 24 h), which were analyzed by reversed phase high-performance liquid chromatography (RP-HPLC), FIG. 3G shows cleavages of the self-assembled nanoparticles (LT-NPs) after enzymatic reaction with cathepsin B for 24 hours, which were analyzed using a fluorescence spectrophotometer (F-7000, Hitachi), and FIG. 3H shows the amounts of reactive oxygen species (ROS) generated from VPF, LT-NPs(-Cat-B), LT-NPs(+Cat-B), and LT-NPs(+Cat-B+inhibitor) as a function of laser irradiation time;

DETAILED DESCRIPTION OF THE INVENTION

Figure 1:
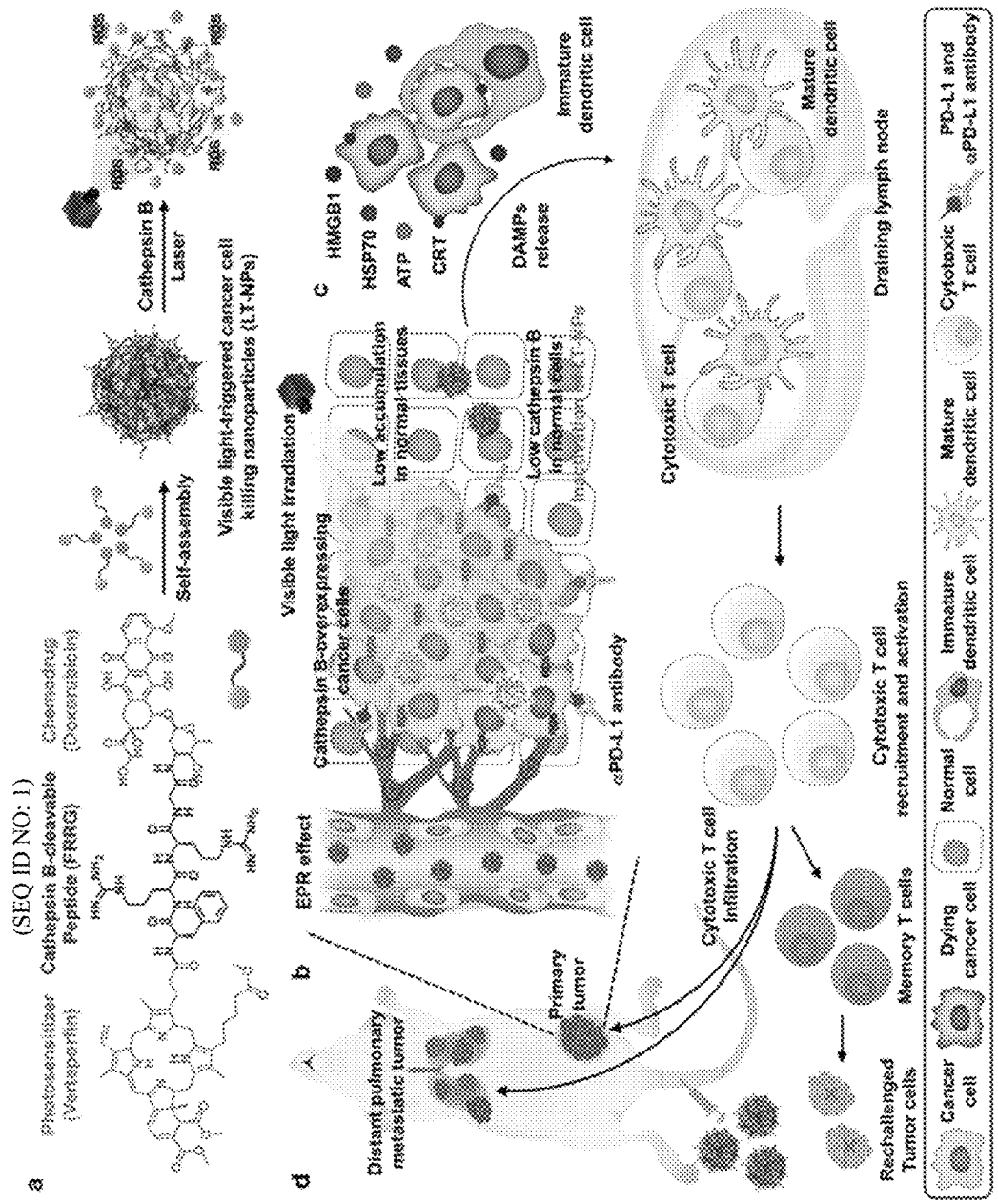
FIG. 1 shows the mechanism of action of immunotherapy by visible light-activatable nanoparticles for cancer immunotherapy according to the present invention. The region a of FIG. 1 shows the formation and activation of self-assembled nanoparticles for cancer immunotherapy and the regions b, c and d of FIG. 1, respectively, show the mechanism of action of self-assembled nanoparticles for cancer immunotherapy in vivo.

The present invention will now be described in detail.

The following abbreviations are used for representative amino acids: Ala (A) for alanine, Ile (I) for isoleucine, Leu (L) for leucine, Met (M) for methionine, Phe (F) for phenylalanine, Pro (P) for proline, Trp (W) for tryptophan, Val (V) for valine, Asn (N) for asparagine, Cys (C) for cysteine, Gln (Q) for glutamine, Gly (G) for glycine, Ser (S) for serine, Thr (T) for threonine, Try (Y) for tyrosine, Asp (D) for aspartic acid, Glu (E) for glutamic acid, Arg (R) for arginine, His (H) for histidine, and Lys (K) for lysine.

As used herein, the term "peptide" refers to a linear molecule in which amino acid residues are joined together by peptide bonds.

The peptide may be prepared by a chemical synthesis method known in the art, particularly a solid-phase synthesis technique (Merrifield, J. Amer. Chem. Soc. 85:2149-54 (1963); Stewart, et al., Solid Phase Peptide Synthesis, 2nd ed., Pierce Chem. Co.: Rockford, 111 (1984)).

One aspect of the present invention is directed to self-assembled nanoparticles including complexes in which a hydrophobic anticancer drug and a photosensitizer are bonded to one end and the other end of a central amphipathic peptide represented by Formula 1, respectively:

(SEQ ID NO: 2)
Xaa1-Arg-Arg-Gly (1)

wherein Xaa is selected from alanine, valine, isoleucine, leucine, methionine, phenylalanine, tyrosine, and tryptophan.

Xaa is not particularly limited as long as it is a hydrophobic amino acid. Xaa is preferably selected from phenylalanine, tyrosine, and tryptophan. Xaa is more preferably phenylalanine (Phe).

The amphipathic peptide is cleaved by "cathepsin B", an enzyme overexpressed in cancer cells. Most preferably, the amphipathic peptide has the sequence set forth in SEQ ID NO: 1.

The self-assembled nanoparticles may have various shapes such as spheres, capsules, and polyhedrons. The self-assembled nanoparticles are preferably spherical in shape. The self-assembled nanoparticles may have an average diameter in the range of 5 to 1,000 nm, preferably 50 to 500 nm, more preferably 50 to 150 nm. Within this range, the self-assembled nanoparticles can stably stay in lesions without being detached therefrom, can be easily degraded and removed in vivo after release of the drug, and are effectively injected into the body through a catheter or syringe needle.

As shown in FIG. 3, the self-assembled nanoparticles are spherical in shape. Due to their shape, the self-assembled nanoparticles can act as single particles despite the presence of the plurality of complexes. Thus, when exposed to external visible light, the self-assembled nanoparticles are easily changed to their active state in situ at the exposed locations and can target lesions more quickly and accurately.

The self-assembled nanoparticles are spherical nanoparticles (prodrug forms) prepared by self-assembly of the complexes in a fluid. Specifically, when the complexes spontaneously form the self-assembled nanoparticles as spherical nanoparticles in a fluid, the anticancer drug as a hydrophobic moiety forms a core and the photosensitizer as a hydrophilic moiety is exposed to the outside of the core to form a surface in contact with the fluid.

The self-assembled nanoparticles of the present invention have advantages in that they are uniform in size in a fluid and stable in vivo.

The photosensitizer, the amphipathic peptide, and the anticancer drug are sequentially bonded in the self-assembled nanoparticles of the present invention. That is, the photosensitizer and the anticancer drug are bonded to one end and the other end of the amphipathic peptide, respectively (FIG. 1 at the region a).

The amphipathic peptide may be prepared by a conventional peptide synthesis method, for example, a chemical synthesis method known in the art, particularly a solid-phase synthesis technique (Merrifield, J. Amer. Chem. Soc. 85:2149-54 (1963); Stewart, et al., Solid Phase Peptide Synthesis, 2nd ed., Pierce Chem. Co.: Rockford, Ill. (1984)). The amphipathic peptide is preferably synthesized by using a solid-phase peptide synthesis (SSPS) technique in which Fmoc-protected amino acid monomers are sequentially attached to a Rink amide resin with C-terminal amide groups. However, there is no particular restriction on the method for synthesizing the amphipathic peptide.

The interaction between the amphipathic peptide and the hydrophobic drug bonded to the amphipathic peptide stabilizes the self-assembled nanoparticles such that the drug does not exhibit toxicity to normal cells. This stabilization leads to a marked improvement in the in vivo structural stability and solubility of the self-assembled nanoparticles while overcoming and solving the side effect problems of conventional anticancer therapeutics.

The amphipathic peptide may be covalently or non-covalently bonded with the hydrophobic anticancer drug and the photosensitizer. Specifically, the hydrophobic anticancer drug and the photosensitizer may be bonded to the N-terminus and C-terminus of the amphipathic peptide, respectively, or vice versa. For example, the hydrophobic anticancer drug and the photosensitizer may be covalently bonded to the amine group of the N-terminal phenylalanine and the carboxyl group of the C-terminal glycine of the amphipathic peptide, respectively, or vice versa.

In a further aspect of the present invention, the hydrophobic anticancer drug or the photosensitizer may be bonded to the amphipathic peptide via a linker. For example, a linker such as a 6-hydrazinopyridine-3-carboxylic acid (Hynic) linker may be introduced to the amine group of the N-terminal phenylalanine or the carboxyl group of the C-terminal glycine of the amphipathic peptide and the hydrophobic anticancer drug or the photosensitizer may be bonded to the linker.

A large length of the amphipathic peptide leads to a considerable reduction in cell penetration efficiency and makes it difficult to form the nanoparticles in a fluid. Meanwhile, a small length of the amphipathic peptide prevents the constituent amino acids from functioning properly.

If any one of the constituent amino acids of the amphipathic peptide is altered, the amphipathic peptide cannot be successfully bonded with the hydrophobic anticancer drug, the resulting conjugates cannot be self-assembled in a solution, failing to form the nanoparticles, or the photosensitizer and the hydrophobic anticancer drug cannot exert their functions properly after degradation of thew self-assembled nanoparticles in tumor cells. For example, when the peptide is cleaved by cathepsin B (in FRRG (SEQ ID NO: 1), "FR" and "RR" are cleavable sites), the self-assembled nanoparticles of the present invention release the hydrophobic anticancer drug and the photosensitizer (hereinafter also referred to as an "activated state"). The hydrophobic anticancer drug is released intact without being unbonded to a portion of the cleaved peptide, unlike conventional hydrophobic anticancer drugs. If the sequence of the amphipathic peptide set forth in SEQ ID NO: 1 is altered, the hydrophobic anticancer drug is not released intact but is released while remaining bonded to one or more amino acid residues (for example, G-DOX and RG-DOX), failing to penetrate the cell nucleus. In this case, the anticancer activity of the anticancer drug may deteriorate considerably or the extracellular release of the anticancer drug may cause side effects.

The conjugates in which the hydrophobic anticancer drug and the photosensitizer are bonded to one end and the other end of the amphipathic peptide having the sequence set forth in SEQ ID NO: 1 undergo self-assembly in a solution to form the spherical nanoparticles (precursor forms of the anticancer drug, inactive state). Due to their shape, the self-assembled nanoparticles may not exhibit any cytotoxicity to normal cells and tissues and may be easily delivered to and accumulated in tumor cells, achieving excellent anticancer efficacy (FIG. 1 at the regions a and b).

If the photosensitizer and the hydrophobic anticancer drug fail to form self-assembled nanoparticles and exist in a mixed state, they are cytotoxic to both normal cells and cancer cells to cause side effects and are much less effective in cancer cell inhibition and cancer immunotherapy than the self-assembled nanoparticles of the present invention.

Accordingly, the photosensitizer has greatly reduced toxicity to normal cells and an enhanced prophylactic or therapeutic effect on cancer cells only.

The hydrophobic anticancer drug is not particularly limited as long as it is hydrophobic. Preferably, the hydrophobic anticancer drug is selected from the group consisting of doxorubicin, cyclophosphamide, mechlorethamine, uramustine, melphalan, chlorambucil, ifosfamide, bendamustine, carmustine, lomustine, streptozocin, busulfan, dacarbazine, temozolomide, thiotepa, altretamine, duocarmycin, cisplatin, carboplatin, nedaplatin, oxaliplatin, satraplatin, triplatin tetranitrate, 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, camptothecin, topotecan, irinotecan, etoposide, teniposide, mitoxantrone, paclitaxel, docetaxel, ixabepilone, vinblastine, vincristine, vindesine, vinorelbine, estramustine, maytansine, mertansine (DM1), DM4, dolastatin, auristatin E, auristatin F, monomethyl auristatin E, monomethyl auristatin F, derivatives thereof, and combinations thereof.

The photosensitizer may be selected from protoporphyrin IX, verteporfin, Foscan, Levulan, Metvix, Hexvix, Purlytin, Photochlor, Lutex, Talaporfin, and mixtures thereof and is preferably verteporfin.

The conjugate in which the hydrophobic anticancer drug and the photosensitizer are bonded to one end and the other end of the amphipathic peptide having the sequence set forth in SEQ ID NO: 1, respectively, is preferably represented by Structural Formula 1:

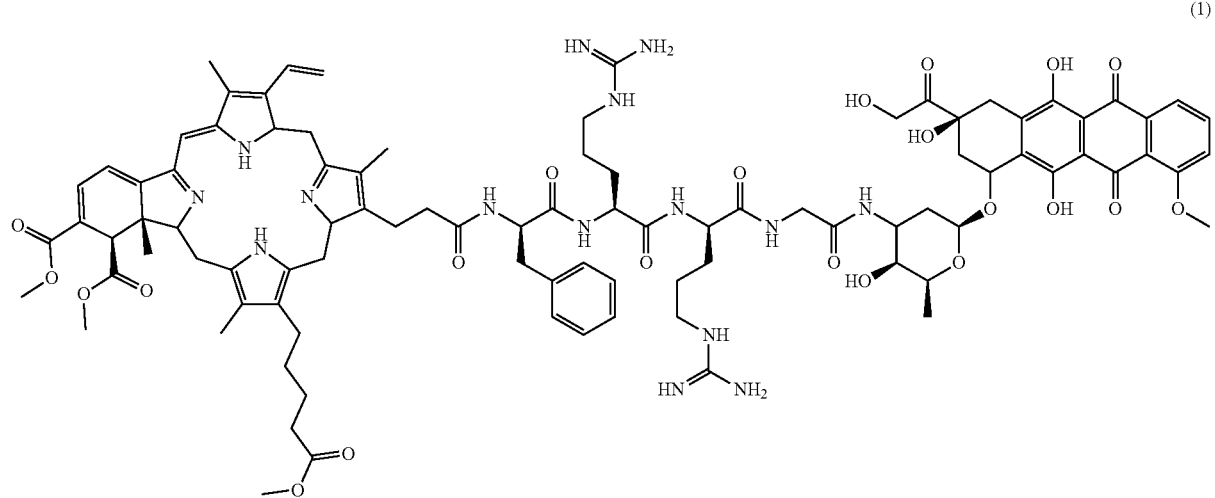 [SMILES: C=CC1=C(C)/C2=C/C3=NC(Cc4[nH]c(c(CCCCC(=O)OC)c4C)CC4N=C(CC1N2)C(C)=C4CCC(=O)N[C@H](Cc1ccccc1)C(=O)N[C@@H](CCCNC(=N)N)C(=O)N[C@H](CCCNC(=N)N)C(=O)NCC(=O)NC1C[C@@H](OC2C[C@](O)(C(=O)CO)Cc4c(O)c5c(c(O)c42)C(=O)c2c(OC)cccc2C5=O)O[C@@H](C)[C@H]1O)[C@@]1(C)C3=CC=C(C(=O)OC)[C@@H]1C(=O)OC]

(1)

The structure of the self-assembled nanoparticles is very stable without causing toxicity in fluids such as saline and body fluids. The self-assembled nanoparticles can be cleaved by cathepsin B overexpressed in cancer cells, and as a result, the liberated anticancer drug and photosensitizer can be activated only at correct target sites (FIG. 1 at the regions of b and c).

Particularly, the photosensitizer present in the self-assembled nanoparticles is not activated upon irradiation with visible light but the photosensitizer liberated by the action of cathepsin B is activated in cancer cells by visible light.

The self-assembled nanoparticles of the present invention accumulate in cancer cells that selectively overexpress cathepsin B, the anticancer drug induces apoptosis, and the photosensitizer generates reactive oxygen species through ex vivo photooxidation when irradiated with visible light, resulting in enhanced apoptosis in cancer cells. Above all, the combined effect of the anticancer drug and the photosensitizer can induce potent immunogenic cell death in cancer cells, achieving a strong cancer immunotherapeutic effect that could not be predicted by conventional anticancer drugs or photosensitizers.

Since the self-assembled nanoparticles of the present invention exhibit strong immunogenic cell death in tumor cells, their superior cancer immunotherapeutic efficacy can be expected. The self-assembled nanoparticles of the present invention were found to be excellent in intracellular uptake and accumulation, specificity, and therapeutic and prophylactic effects on cancer compared to single or combined administration of anticancer drugs.

More specifically, the self-assembled nanoparticles introduced into the body by oral administration, transdermal administration, rectal administration, intravenous injection, intramuscular injection, subcutaneous injection, intrauterine injection, intradural injection or cerebrovascular injection move into cells and are cleaved only in cancer cells containing a large amount of cathepsin B to liberate the anticancer drug and the photosensitizer. The released anticancer drug can exert its own therapeutic effect on cancer cells. At this time, external visible light irradiated onto a lesion activates the liberated photosensitizer. As a result, immunogenic cell death in cancer cells can be effectively induced together with the anticancer activity of the anticancer drug (FIG. 1 at the regions b and c).

Since the self-assembled nanoparticles are not activated even when exposed to visible light, they do not induce apoptosis in normal cells expressing a low level of cathepsin B. Furthermore, the self-assembled nanoparticles are stable materials that do not exhibit any toxicity to normal cells.

Due to the structure of the complexes, the self-assembled nanoparticles simultaneously release the anticancer drug and the photosensitizer in cancer cells to effectively induce immunogenic cell death in cancer cells, thus being effective in preventing or treating cancer.

The self-assembled nanoparticles of the present invention are not limited in their clinical use because they exert tumor tissue-specific activity, stable cytotoxicity, and other effects despite the absence of any carrier.

Specifically, the self-assembled nanoparticles of the present invention have the following advantages: (i) the self-assembled nanoparticles are made spherical by self-assembly without the need for any type of nanocarrier and are usually present in the form of prodrugs that do not exhibit any toxicity to cells, causing no side effects; (ii) the self-assembled nanoparticles have specific activity against tumor cells under visible light irradiation; (iii) the self-assembled nanoparticles exhibit enhanced anticancer activity even at a low concentration; and (iv) the self-assembled nanoparticles can induce strong immunogenic cell death in cancer cells, thereby maximizing their therapeutic efficacy for cancer.

Various therapeutic agents have been recently developed to solve the problem of resistance of tumor cells but are provided only in the form of simple conjugates with anticancer drugs. These therapeutic agents greatly lower the growth of tumor cells but should be used for a long time to treat cancer. Further, combined administration with immune checkpoint inhibitors is insufficient for complete removal of tumors. In contrast, combined administration of the self-assembled nanoparticles according to the present invention with an immune checkpoint inhibitor can activate immune cells to induce complete apoptosis in cancer tissues despite a reduced frequency of administration. Therefore, the use of the self-assembled nanoparticles according to the present invention can produce a synergistic effect greater than expected.

The self-assembled nanoparticles of the present invention can suppress cancer metastasis during their administration. After killing of cancer tissues, the self-assembled nanoparticles of the present invention can improve immunogenicity against cancer to suppress cancer recurrence.

That is, the self-assembled nanoparticles of the present invention can achieve unexpected therapeutic and prophylactic effects on cancer and multifunctional therapeutic or prophylactic effects on cancer, including inhibitory effects on cancer recurrence and metastasis, compared to combined administration with conventional peptide-anticancer drug complexes or immune checkpoint inhibitors.

Another aspect of the present invention is directed to a pharmaceutical composition for preventing or treating cancer including the self-assembled nanoparticles as active ingredients.

The cancer is intended to include general cancer diseases, including solid tumors and blood born tumors, and may be selected from the group consisting of brain tumor, benign astrocytoma, malignant astrocytoma, pituitary adenoma, meningioma, central nervous system lymphoma, oligodendroglioma, craniopharyngioma, ependymoma, brain stem tumor, head and neck tumor, laryngeal cancer, oropharyngeal cancer, nasal cavity/paranasal sinus cancer, nasopharyngeal cancer, salivary gland cancer, hypopharyngeal cancer, thyroid cancer, oral cavity cancer, chest tumor, small cell lung cancer, non-small cell lung cancer, thymus cancer, mediastinal tumor, esophageal cancer, breast cancer, male breast cancer, abdominal tumor, stomach cancer, liver cancer, gall bladder cancer, biliary tract cancer, pancreatic cancer, small intestine cancer, large intestine cancer, anal cancer, bladder cancer, kidney cancer, prostate cancer, testicular cancer, uterine cancer, cervical cancer, endometrial cancer, ovarian cancer, uterine sarcoma, squamous cell carcinoma, skin cancer, resistant cancers, recurrent cancers, metastatic cancers, and combinations thereof.

The present invention also provides use of the pharmaceutical composition for preventing or treating the diseases listed above, use of the drug complexes or the self-assembled nanoparticles for the preparation of a medicament for preventing or treating the diseases listed above, and a method for preventing or treating the diseases listed above including administering a pharmaceutically acceptable amount of the self-assembled nanoparticles to a mammal, including a human.

The self-assembled nanoparticles of the present invention may be added to a food or beverage for the purpose of preventing or ameliorating cancer.

As used herein, the term "resistant cancer" refers to a cancer that exhibits extremely low sensitivity to cancer therapies, for example, radiotherapy such as photodynamic therapy, and whose symptoms are not ameliorated, alleviated, mitigated or treated by the therapy. The resistant cancer may be originally resistant to a specific therapy. Alternatively, the resistant cancer may not originally resistant to a specific therapy but no longer exhibit sensitivity to the same therapy due to genetic mutations in cancer cells caused by long-term treatment.

As used herein, the term "metastatic cancer" refers to a cancer caused by cancer cells that have spread from the primary organ to a distant organ and proliferated in the distant organ. The cancer spread to other parts of the body can be broadly divided into: direct invasion of cancer tissues grown from the primary cancer to a nearby organ; and metastasis to a distant organ through blood or lymphatic vessels. The metastatic cancer is preferably intended to include cancers that have metastasized from other primary cancers to the organs described above, but is not limited thereto.

As used herein, the term "recurrent cancer" refers to a cancer that has come back at the same site as the original cancer after a patient has been judged to be cured by initial treatment. For the purposes of the present invention, the recurrent cancer may be the recurrence of cancer via epithelial-mesenchymal transition but is not limited thereto.

The pharmaceutical composition of the present invention may further include an immune checkpoint inhibitor.

As used herein, the term "immune checkpoint" refers collectively to proteins involved in inducing stimulatory or inhibitory signals of immune responses on the surface of immune cells. Cancer cells evade the immune system's surveillance by manipulating immune checkpoints such that stimulation of immune responses and the resulting inhibition of cancer cells do not proceed properly. The immune checkpoint protein is preferably a PD-1 antagonist, a PD-L1 antagonist, a PD-L2 antagonist, a CD27 antagonist, a CD28 antagonist, a CD70 antagonist, a CD80 antagonist, a CD86 antagonist, a CD137 antagonist, a CD276 antagonist, a KIRs antagonist, a LAG3 antagonist, a TNFRSF4 antagonist, a GITR antagonist, a GITRL antagonist, a 4-1BBL antagonist, a CTLA-4 antagonist, an A2AR antagonist, a VTCN1 antagonist, a BTLA antagonist, an IDO antagonist, a TIM-3 antagonist, a VISTA antagonist, a KLRA antagonist or a combination thereof, but is not limited thereto. The immune checkpoint protein is more preferably a PD-1 antagonist, a PD-L1 antagonist or a PD-L2 antagonist, most preferably a PD-1 antagonist or a PD-L1 antagonist.

The immune checkpoint inhibitor is an antagonist or antibody that target the immune checkpoint protein. The immune checkpoint inhibitor enhances a protein stimulating an immune response or blocks a protein suppressing an immune response to achieve an anticancer effect due to the immune response. Immune checkpoint inhibitors have fewer side effects such as vomiting and hair loss and better therapeutic effects than general cytotoxic anticancer drugs. In addition to these advantages, immune checkpoint inhibitors maintain their therapeutic effects for a long time even after drug administration is stopped because they use immune response systems with good memory ability. However, there has been no report about the enhancement of anticancer effects through the combination of the self-assembled nanoparticles of the present invention and an immune checkpoint inhibitor. Under such circumstances, the present inventors have tried to use an immune checkpoint inhibitor in order to enhance the anticancer effect of the self-assembled nanoparticles. Accordingly, another technical feature of the present invention is that the self-assembled nanoparticles are used in combination with an immune checkpoint inhibitor to provide their medical use for preventing or treating cancer.

The self-assembled nanoparticles of the present invention and the immune checkpoint inhibitor are preferably mixed in a weight ratio ranging from 1:0.1 to 1:0.8. Outside this range, the inhibitory effect of the self-assembled nanoparticles on cancer and the efficacy of the self-assembled nanoparticles in activating immune cell are greatly reduced.

As used herein, the term "including as active ingredients" means that the self-assembled nanoparticles are present in an amount sufficient to achieve therapeutic or prophylactic efficacy or activity against cancer, resistant cancer, recurrent cancer or metastatic cancer.

The amount of the self-assembled nanoparticles as active ingredients in the pharmaceutical composition for preventing or treating cancer is, for example, at least 0.001 mg/kg, preferably at least 0.1 mg/kg, more preferably at least 10 mg/kg, even more preferably at least 100 mg/kg, still more preferably at least 250 mg/kg, and most preferably at least 0.1 g/kg. Since the self-assembled nanoparticles are prepared in the form of prodrugs in a solution and are present very stable without causing toxicity to cells, they do not cause side effects in humans even when administered in an excessive amount. Accordingly, the upper limit for the amount of the self-assembled nanoparticles in the composition of the present invention can be determined within an appropriate range by those skilled in the art.

The pharmaceutical composition may further include one or more pharmaceutically suitable and physiologically acceptable adjuvants, in addition to the active ingredients. Examples of available adjuvants include excipients, disintegrants, sweeteners, binders, encapsulating agents, swelling agents, lubricants, glidants, and flavoring agents.

For administration, the pharmaceutical composition may be formulated with one or more pharmaceutically acceptable carriers.

For example, the pharmaceutical composition may be formulated into a granule, powder, tablet, coated tablet, capsule, suppository, solution, syrup, juice, suspension, emulsion, drop or injectable solution. For example, the pharmaceutical composition may be formulated into a tablet or capsule. For this formulation, the active ingredients may be combined with an oral, nontoxic, pharmaceutically acceptable inert carrier such as ethanol, glycerol or water. If desired or necessary, the active ingredients may be mixed with one or more suitable adjuvants selected from the group consisting of binders, lubricants, disintegrants, and color developing agents. Suitable binders include, but are not limited to, natural sugars such as starch, gelatin, glucose, and beta-lactose, natural and synthetic gums such as corn sweeteners, acacia, tragacanth, and sodium oleate, sodium stearate, magnesium stearate, sodium benzoate, sodium acetate, and sodium chloride. Suitable disintegrants include, but are not limited to, starch, methylcellulose, agar, bentonite, and xanthan gum.

The composition may be formulated into a solution. In this case, the composition may further include a pharmaceutically acceptable carrier. Suitable pharmaceutically acceptable carriers are sterile biocompatible carriers and examples thereof include saline, sterilized water, Ringer's solution, buffered saline, albumin injectable solution, dextrose solution, maltodextrin solution, glycerol, and ethanol, which may be used alone or as a mixture of two or more thereof. If necessary, the composition may further include other general additives such as antioxidants, buffers, and bacteriostatic agents. Diluents, dispersants, surfactants, binders, and lubricants may be further added to prepare injectable formulations (such as aqueous solutions, suspensions, and emulsions), pills, capsules, granules, and tablets.

The composition can be formulated according to the type of diseases or the kind of ingredients in accordance with any suitable method known in the art, preferably any of the methods disclosed in Remington's Pharmaceutical Science, Mack Publishing Company, Easton Pa.

The pharmaceutical composition may be administered orally or parenterally. The pharmaceutical composition is administered parenterally, for example, intravenously, subcutaneously, intramuscularly, intraperitoneally, transdermally or intratumorally but is preferably administered orally.

A suitable dosage of the pharmaceutical composition may vary depending on factors such as formulation, mode of administration, patient's age, weight, sex, pathological condition, and diet, time of administration, route of administration, excretion rate, and responsiveness. A skilled physician can easily determine and prescribe a dose of the pharmaceutical composition effective for desired treatment and prevention. According to a preferred embodiment, the pharmaceutical composition is administered in a daily dose of 0.01 to 100 mg/kg, preferably 0.5 to 10 mg/kg. The pharmaceutical composition is more preferably administered in single or divided doses per day.

The pharmaceutical composition can be formulated with one or more pharmaceutically acceptable carriers and/or excipients in accordance with methods that can be easily carried out by those skilled in the art. The pharmaceutical composition can be provided in unit dosage forms or dispensed in multi-dose containers. The formulation may be in the form of a solution, suspension or emulsion in an oil or aqueous medium or may be in the form of an extract, powder, granule, tablet or capsule. The formulation may further include a dispersant or a stabilizer.

The self-assembled nanoparticles and the immune checkpoint inhibitor may be administered simultaneously, sequentially or separately to a subject to treat or prevent cancer. The "simultaneous" administration means that the self-assembled nanoparticles and the immune checkpoint inhibitor are administered at one time by intraperitoneal injection.

The "sequential" administration means that the self-assembled nanoparticles and the immune checkpoint inhibitor are administered in a relatively continuous mode by different injection methods but are administered while allowing the shortest possible time for the administration intervals. The "separate" administration means that the self-assembled nanoparticles and the immune checkpoint inhibitor are administered at regular time intervals. The modes of administration of the self-assembled nanoparticles and the immune checkpoint inhibitor can be appropriately selected by those skilled in the art taking into consideration their therapeutic efficacy and side effects in patients.

The present invention will be more specifically explained with reference to the following examples. However, it will be obvious to those skilled in the art that these examples are provided for illustrative purposes only and are not intended to limit the scope of the invention.

EXAMPLE 1

Synthesis of Visible Light-Activatable Nanoparticles (LT-NPs) for Immunotherapy

Synthesis of Amphipathic Peptide

The amphipathic peptide having the sequence set forth in SEQ ID NO: 1 was prepared according to a solid-phase peptide synthesis method known in the art. Specifically, the amphipathic peptide was synthesized by coupling amino acids one by one from the C-terminus following Fmoc solid phase peptide synthesis (SPPS) using ASP48S (Peptron, Inc., Daejeon, Korea). A resin attached with the first amino acid from the C-terminus of the amphipathic peptide was used: for example, $NH_2$-Gly(Boc)-2-chloro-trityl resin All amino acids used as raw materials for peptide synthesis were N-terminally Fmoc protected and the residues were protected with Trt, Boc, t-butylester (t-Bu) or 2,2,4,6,7-pentamethyl dihydrobenzofuran-5-sulfonyl (Pbf), all of which were removed in acid: for example, Fmoc-Phe-OH and Fmoc-Arg(Pbf)-OH.

2-(1H-benzotriazol-1-yl)-1,1,3,3-tetamethylaminium hexafluorophosphate (HBTU)/N-hydroxybenzotriazole (HOBt)/4-methylmorpholine (NMM) was used as a coupling reagent. Fmoc was removed with 20% piperidine in DMF.

The synthesized peptide was detached from the resin and the protecting groups of the residues were removed using a cleavage cocktail (trifluoroacetic acid (TFA)/triisopropylsilane (TIS)/ethanedithiol (EDT)/$H_2O$=92.5/2.5/2.5/2.5).

The protected starting amino acid bound to the solid support was sequentially allowed to react with the corresponding amino acids. The reaction product was washed with a solvent and deprotected. The above procedure was repeated to synthesize the peptide. The synthesized peptide was detached from the resin, purified by HPLC, determined by MS whether it was successfully synthesized, and lyophilized.

Figure 2:
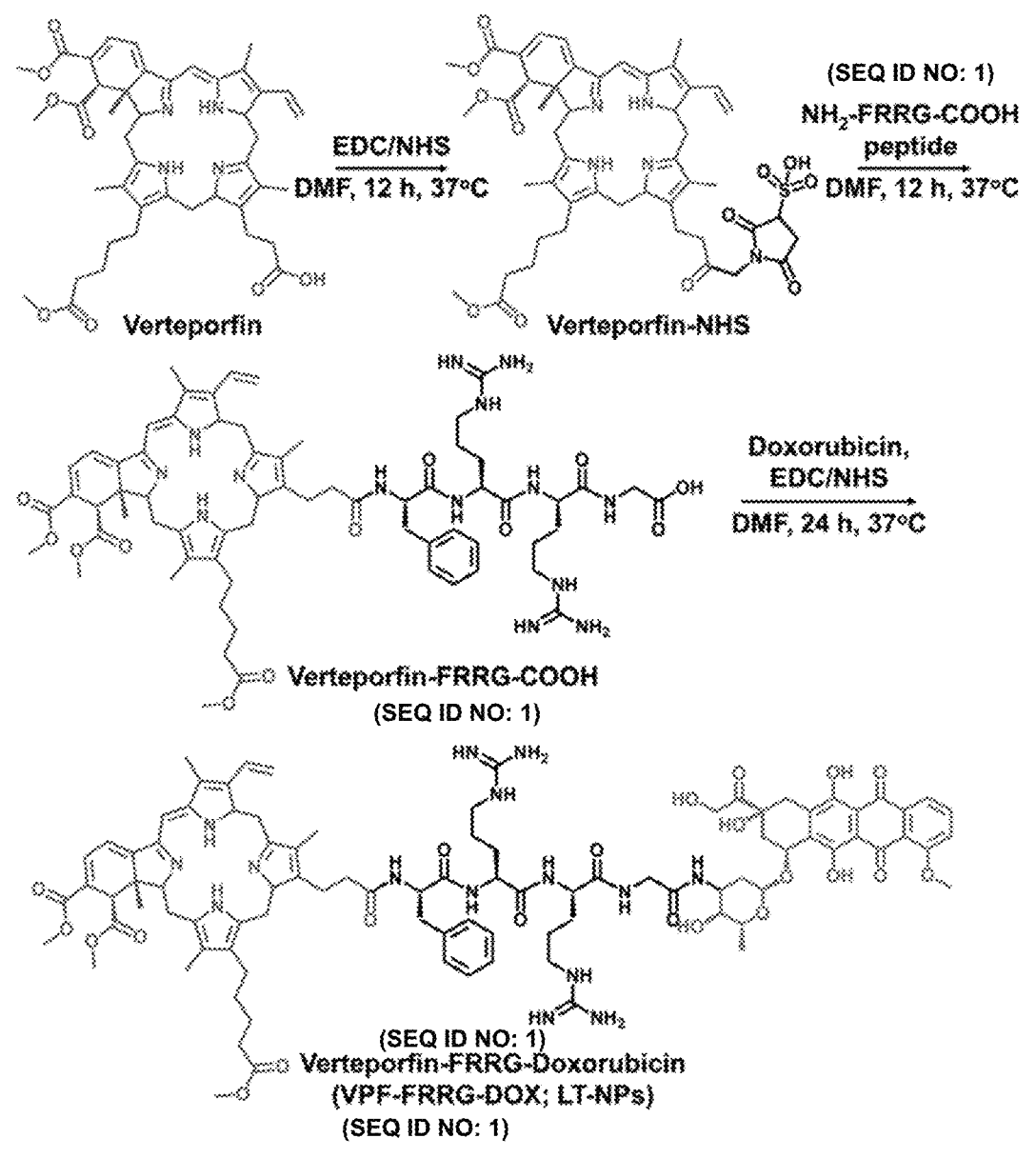

Preparation of Self-Assembled Nanoparticles (LT-NPs) Composed of VPF-FRRG(SEQ ID NO: 1)-DOX Self-assembled nanoparticles (LT-NPs) were synthesized through a two-step amidation reaction (FIG. 2). First, verteporfin (VPF) (1 g, 1.33 mmol), EDC (0.75 g, 3.93 mmol), and NHS (0.5 g, 6.52 mmol) were dissolved in 100 mL of anhydrous dimethylformamide (DMF) and stirred at 37° C. for 12 h to synthesize VPF-NHS. The VPF-NHS was purified by high performance liquid chromatography (HPLC) using ACN/$H_2O$ (concentration gradients=80:20-20:80, 30 min). The purified VPF-NHS (1 g, 1.15 mmol) was mixed with DMF (100 mL) and $NH_2$-FRRG(SEQ ID NO: 1)-COOH (1 g, 1.87 mmol) was added thereto. The mixture was allowed to react at 37° C. for 12 h to synthesize VPF-FRRG(SEQ ID NO: 1)-COOH.

After purification by HPLC, the VPF-FRRG(SEQ ID NO: 1)-COOH (800 mg, 0.62 mmol), doxorubicin (660 mg, 1.22 mmol), and EDC (0.37 g, 1.94 mmol) were mixed together to synthesize VPF-FRRG(SEQ ID NO: 1)-DOX (LT-NPs). The VPF-FRRG(SEQ ID NO: 1)-DOX (LT-NPs) was added to 100 mL of anhydrous DMF and NHS (0.25 g, 3.26 mmol) was added thereto. The mixture was stirred at 37° C. for 24 h. The VPF-FRRG(SEQ ID NO: 1)-DOX (LT-NPs) was purified by high performance liquid chromatography (HPLC) using ACN/$H_2O$ (concentration gradients=(80:20-20:80, 30 min). The VPF-FRRG(SEQ ID NO: 1)-DOX (LT-NPs) was determined to have a final purity of >99%.

EXPERIMENTAL EXAMPLE 1

Size Analysis of the Self-Assembled Nanoparticles (LT-NPs)

The self-assembled nanoparticles (LT-NPs) prepared in Example 1 were diluted with saline to a concentration of 1 mg/mL and their particle size was analyzed by dynamic light scattering (DLS; Zetasizer Nano ZS, Malvern Instruments).

Figure 3A:
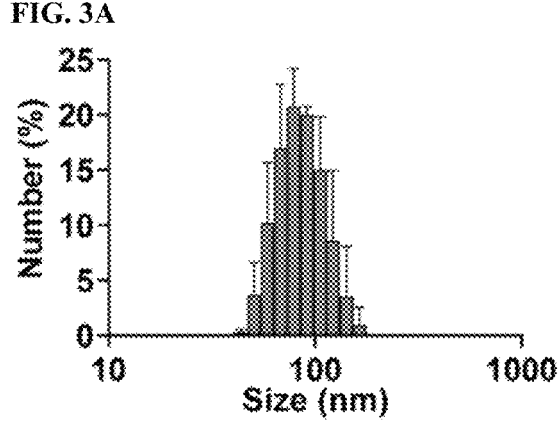
FIGS. 3A-3H show the results of analyzing the physical/chemical properties of self-assembled nanoparticles (LT-NPs) prepared in Example 1.

FIG. 3A shows the size of the self-assembled nanoparticles (LT-NPs) measured by dynamic light scattering (DLS). The graph revealed that the self-assembled nanoparticles (LT-NPs) had an average particle diameter of 87 nm.

EXPERIMENTAL EXAMPLE 2

Morphological Analysis of the Self-Assembled Nanoparticles (LT-NPs)

The self-assembled nanoparticles (LT-NPs) prepared in Example 1, doxorubicin (DOX), and verteporfin (VPF) were used as samples. 1 mg of each sample was mixed with physiological saline (1 mL). The mixture solution was observed with a transmission electron microscope (TEM; CM-200, Phillips). The self-assembled nanoparticles (LT-NPs) were mixed with cathepsin B (Cat-B) protease (50

μg/mL). The mixture was allowed to react for 24 h. The reaction product (LT-NPs+Cat-B) was observed with a transmission electron microscope.

Figure 3B:
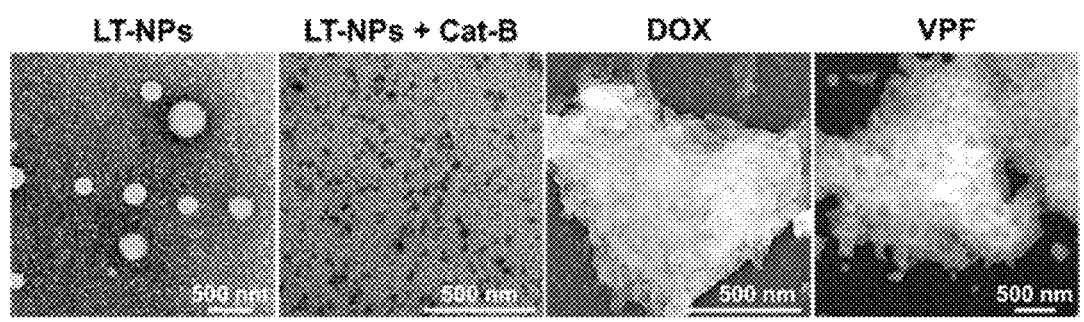

FIG. 3B shows transmission electron microscopy images revealing the morphologies of the self-assembled nanoparticles (LT-NPs), doxorubicin, and verteporfin (VPF). As shown in FIG. 3B, the self-assembled nanoparticles (LT-NPs) were dispersed without aggregation in saline. In addition, the self-assembled nanoparticles (LT-NPs) were degraded by cathepsin B present in cancer cells and existed in an activated state where anticancer effects were achieved.

Each of the anticancer drug doxorubicin (DOX) and the photosensitizer verteporfin (VPF) aggregated and existed in the form of very large particles (>500 nm).

EXPERIMENTAL EXAMPLE 3

Stability Analysis of the Self-Assembled Nanoparticles (LT-NPs)

In this example, the stability of the self-assembled nanoparticles (LT-NPs) in a body fluid was determined. To this end, the self-assembled nanoparticles (LT-NPs) were stored in plasma samples from BALB/c mice for 0, 1, 3, 6, 24, 48, and 72 h and their sizes were measured by dynamic light scattering (DLS).

Figure 3C:
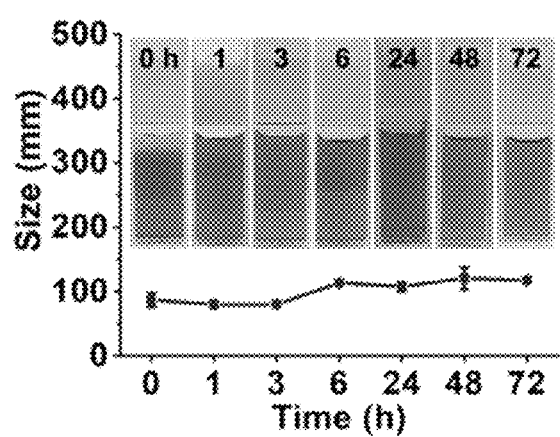

FIG. 3C shows time-dependent changes in the size of the self-assembled nanoparticles (LT-NPs) in mouse plasma. As shown in FIG. 3C, significant differences in the size of the self-assembled nanoparticles (LT-NPs) were not observed up to 72 h, indicating that the self-assembled nanoparticles (LT-NPs) stably maintained their morphology in the body fluid.

EXPERIMENTAL EXAMPLE 4

Structural Analysis of the Self-Assembled Nanoparticles (LT-NPs)

The self-assembled nanoparticles (LT-NPs) prepared in Example 1, doxorubicin (DOX), verteporfin (VPF), and a mixture of doxorubicin (DOX) and verteporfin (VPF) were used as samples. Each sample (10 μM) was mixed with physiological saline (1 mL). The mixture solution was analyzed using a UV spectrophotometer (Agilent care 300; Agilent Technologies) and a fluorescence spectrophotometer (F-7000, Hitachi).

Figure 3D:
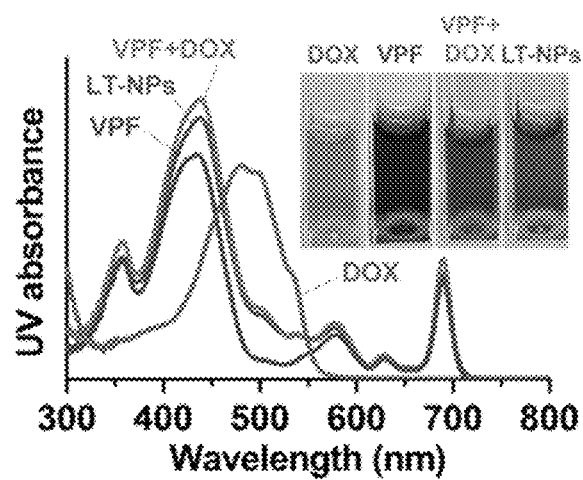
Figure 3E:
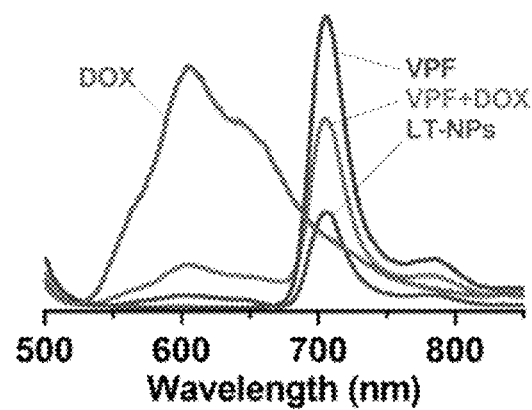

FIG. 3D shows UV spectra of the self-assembled nanoparticles (LT-NPs), doxorubicin (DOX), verteporfin (VPF), and the mixture of doxorubicin (DOX) and verteporfin (VPF) and FIG. 3E shows the fluorescence intensities of the self-assembled nanoparticles (LT-NPs), doxorubicin (DOX), verteporfin (VPF), and the mixture of doxorubicin (DOX) and verteporfin (VPF).

As shown in FIGS. 3D and 3E, the spectra of the self-assembled nanoparticles (LT-NPs) showed peaks corresponding to both doxorubicin and verteporfin.

EXPERIMENTAL EXAMPLE 5

Reactivity Analysis of the Self-Assembled Nanoparticles (LT-NPs)

In this example, the activation of the self-assembled nanoparticles (LT-NPs) by cathepsin B (Cat-B) was determined. To this end, an experimental sample and a comparative sample were prepared and allowed to react in an incubator at 37° C. Specific cleavages by cathepsin B were evaluated at reaction times of 0, 9, and 24 h by reversed phase high-performance liquid chromatography (RT-HPLC).

Experimental sample (Cat-B): The self-assembled nanoparticles (LT-NPs) (10 μM) prepared in Example 1 were mixed with a 2-(N-morpholine)-ethanesulphonic acid (MES) buffer (200 μL) containing cathepsin B (10 μg).

Comparative sample (Cat-B+inhibitor): The self-assembled nanoparticles (LT-NPs) (10 μM) prepared in Example 1 were mixed with a 2-(N-morpholine)-ethanesulphonic acid (MES) buffer (200 μL) containing cathepsin B (10 μg) and a cathepsin B inhibitor (Z-FA-FMK, 50 μM).

Figure 3F:
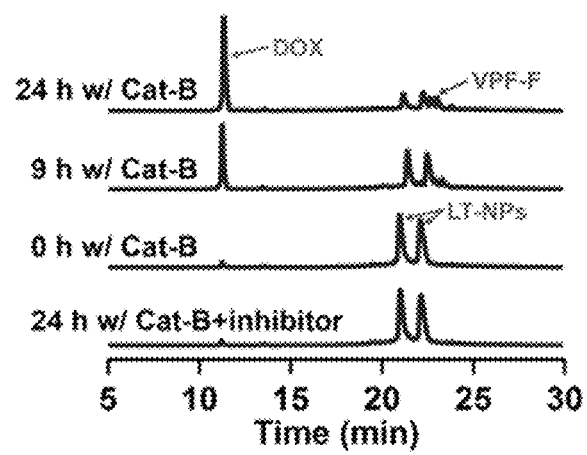
Figure 3G:
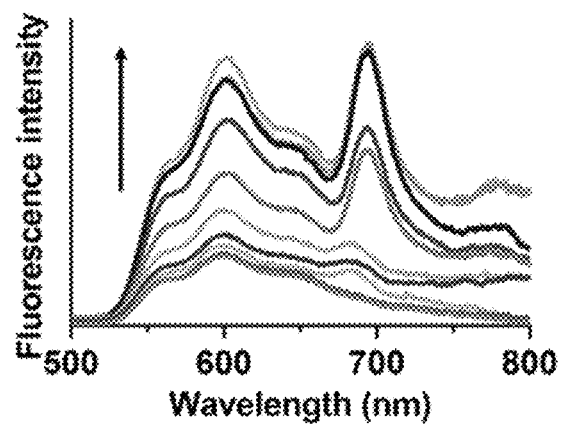

FIG. 3F shows cleavages of the self-assembled nanoparticles (LT-NPs) after enzymatic reaction with cathepsin B for different times (0, 9, and 24 h), which were analyzed by reversed phase high-performance liquid chromatography (RP-HPLC) and FIG. 3G shows cleavages of the self-assembled nanoparticles (LT-NPs) after enzymatic reaction with cathepsin B for 0-72 h, which were analyzed using a fluorescence spectrophotometer (F-7000, Hitachi).

As shown in FIGS. 3F and 3G, the self-assembled nanoparticles (LT-NPs) were cleaved by cathepsin B to release doxorubicin and the photosensitizer.

EXPERIMENTAL EXAMPLE 6

Generation of Reactive Oxygen Species (ROS) from the Self-Assembled Nanoparticles (LT-NPs)

ROS generation was analyzed by RNO test, where bleaching of N-nitrosodimethylaniline (RNO) by ROS was observed as a decrease in absorbance at 440 nm.

To determine the reactivity of the self-assembled nanoparticles (LT-NPs) to visible light, experimental samples and a comparative sample were prepared as follows. Each sample was mixed with a 10 μM RNO standard solution and irradiated with visible light using a 671 nm laser (SDL-671 series, Shanghai Dream Laser Technology Co., Ltd.) at a power of 40 mW for 250 sec. Absorbances were measured at 440 nm over time while being irradiated with visible light.

Control sample (VPF, control): Verteporfin (VPF) (10 μM) was mixed with physiological saline (1 mL).

Experimental sample 1 (LT-NPs(-Cat-B)): The self-assembled nanoparticles (LT-NPs) (10 μM) prepared in Example 1 were mixed with physiological saline (1 mL).

Experimental sample 2 (LT-NPs(+Cat-B)): The self-assembled nanoparticles (LT-NPs) (10 μM) prepared in Example 1 were mixed with distilled water (200 μL) containing cathepsin B (10 μg) and 1.2 mM histidine.

Comparative sample (LT-NPs(+Cat-B+inhibitor)): The self-assembled nanoparticles (LT-NPs) (10 μM) prepared in Example 1 were mixed with distilled water (200 μL) containing cathepsin B (10 μg), a cathepsin B inhibitor (Z-FA-FMK, 50 μM), and 1.2 mM histidine.

Statistics

Statistical analysis was done using one-way ANOVA test to determine significant differences in the mean value between groups. * indicates a significant difference at $p<0.05$,  indicates a significant difference at $p<0.01$, * indicates a significant difference at $p<0.001$, and N.S indicates no significant difference. Error bars indicate standard deviation.

Figure 3H:
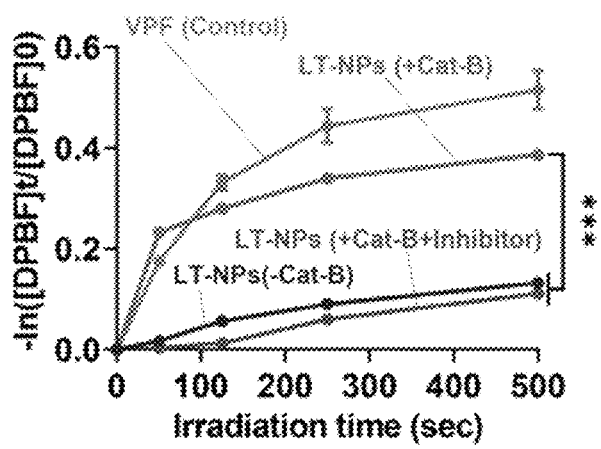

FIG. 3H shows the amounts of reactive oxygen species (ROS) generated from VPF, LT-NPs(-Cat-B), LT-NPs(+Cat-B), and LT-NPs(+Cat-B+inhibitor) as a function of laser irradiation time.

First, the absorbance before laser irradiation was defined as 1 and reduction rates of the absorbance values measured at 440 nm with respect to the absorbance before laser irradiation were calculated. The calculated values were transformed into negative natural logs (−In(y)), which were then multiplied by 100. The resulting values were defined as the amounts of reactive oxygen species generated. The data were plotted versus time.

The ROS generation efficiencies of the self-assembled nanoparticles with respect to laser irradiation time were represented by slopes, which were compared with the ROS generation quantum efficiency at a laser irradiation time of 0 to determine relative ROS generation quantum efficiencies.

The self-assembled nanoparticles (LT-NPs) in a stable state were hardly reactive with visible light. In contrast, when cleaved with cathepsin B, a significantly increased amount of ROS was generated. The level corresponded to 80% of that from verteporfin (VPF).

EXPERIMENTAL EXAMPLE 7

Specificity of the Self-Assembled Nanoparticles (LT-NPs) to Cancer Cells

The following experiment was conducted to evaluate the intracellular behaviors of the self-assembled nanoparticles (LT-NPs). First, $1\times10^5$ CT26 cells or H9C2 cells were plated in a 35 mm cell culture dish, treated with the self-assembled nanoparticles (LT-NPs, 5 µM) prepared in Example 1, and cultured for 24 h. Thereafter, cells were washed with Dulbecco's PBS (DPBS), fixed in 4% formaldehyde for 10 min, stained with 4',6-diamidino-2-phenylindole (DAPI) for 5 min, and analyzed with a Leica TCS SP8 confocal microscope (Leica Microsystems GmbH).

Figure 4A:
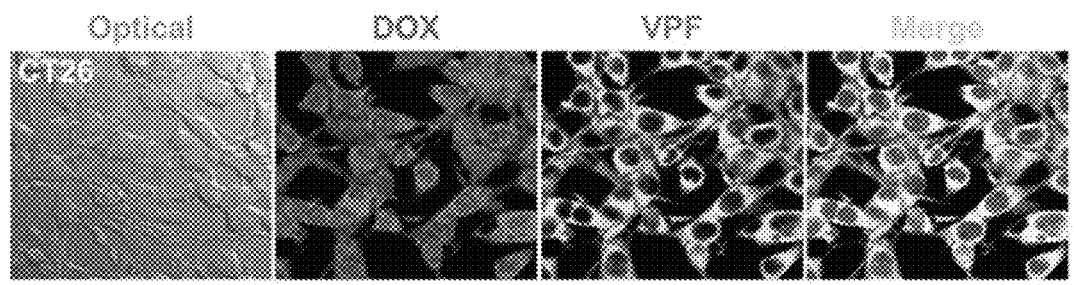
FIG. 4A shows fluorescence microscopy images of CT26 cancer cells after treatment with self-assembled nanoparticles (LT-NPs)
Figure 4B:
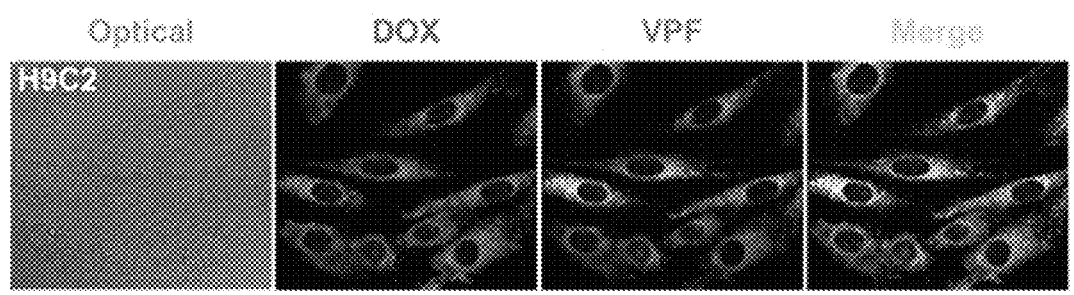
FIG. 4B shows fluorescence microscopy images of H9C2 cardiac cells after treatment with self-assembled nanoparticles (LT-NPs)
Figure 4C:
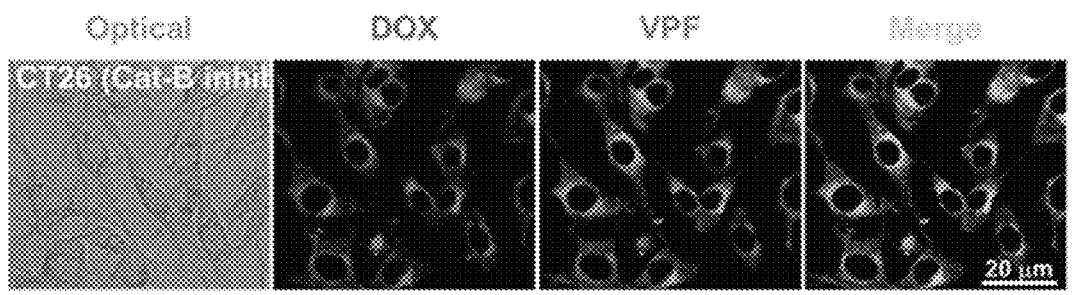
FIG. 4C shows fluorescence microscopy images of CT26 cells, which had been treated with a cathepsin B inhibitor, after treatment with self-assembled nanoparticles (LT-NPs)

FIG. 4A shows fluorescence microscopy images of CT26 cancer cells after treatment with the self-assembled nanoparticles (LT-NPs), FIG. 4B shows fluorescence microscopy images of H9C2 cells after treatment with the self-assembled nanoparticles (LT-NPs), and FIG. 4C shows fluorescence microscopy images of CT26 cells, which had been treated with a cathepsin B inhibitor, after treatment with the self-assembled nanoparticles (LT-NPs). In these images, doxorubicin (DOX) and verteporfin (VPF) are colored in red and green, respectively.

As shown in FIGS. 4A to 4C, the self-assembled nanoparticles (LT-NPs) were observed in both cardiomyocytes (H9C2) and cancer cells (CT26). However, doxorubicin (red) was observed in the nucleus of cancer cells (CT26) and verteporfin (green) was observed in the cytoplasm of cancer cells (CT26), unlike in cardiomyocytes (H9C2).

That is, the inventive self-assembled nanoparticles (LT-NPs) were cleaved specifically to cancer cells and degraded into doxorubicin with anticancer effects and verteporfin. The doxorubicin moved into the cell nucleus where it showed anticancer effects, and the verteporfin remained in the cytoplasm and induced apoptosis in cancer cells when irradiated with visible light.

In the cancer cells (CT26) treated with the cathepsin B inhibitor, the self-assembled nanoparticles (LT-NPs) were not degraded and remained stable in the cytoplasm.

The specific activity of the inventive self-assembled nanoparticles (LT-NPs) against cancer cells and the presence of the inventive self-assembled nanoparticles (LT-NPs) in a stable state in normal cells indicate non-toxicity of the self-assembled nanoparticles (LT-NPs) to normal cells.

EXPERIMENTAL EXAMPLE 8

Analysis of Ability of the Self-Assembled Nanoparticles (LT-NPs) to Kill Cancer Cells After CT26 cells were plated in a 96-well plate at a density of $5\times10^3$ cells/well, the wells were treated with doxorubicin (DOX) (0, 0.01, 0.1, 1, and or 10 µM), verteporfin (VPF) (0, 0.01, 0.1, 1, and 10 µM), mixtures thereof (DOX+VPF), and the self-assembled nanoparticles (LT-NPs) (0, 0.01, 0.1, 1, and 10 µM). After culture for 24 h, cells were exposed by irradiation with visible light using a 671 nm laser at 40 mW for 250 sec. Then, a cell culture medium containing 10 µg of CCK solution was added to each well. Cells were further cultured for 20 min and the absorbance of the 96-well plate was measured at 450 nm on a VERSAmax™ microplate reader (Molecular Devices Corp., Sunnyvale, Calif.).

The degrees of apoptosis and necrosis of cancer cells were quantitatively analyzed to accurately evaluate the anticancer effect of the self-assembled nanoparticles (LT-NPs). First, CT26 cells treated with doxorubicin (DOX), verteporfin (VPF), a mixture of doxorubicin and verteporfin (VPF+DOX) or the self-assembled nanoparticles (LT-NPs) and a laser were prepared as above and treated with 5 µg of Annexin V-FITC and 10 µg of PI solution for 10 min. Then, cells were cultured with a cell fixative for 10 min and further cultured with DAPI for 20 min. The degrees of apoptosis and necrosis were quantitatively analyzed using a flow cytometer (BD FACSVerse, BD bioscience, USA).

Figure 4D:
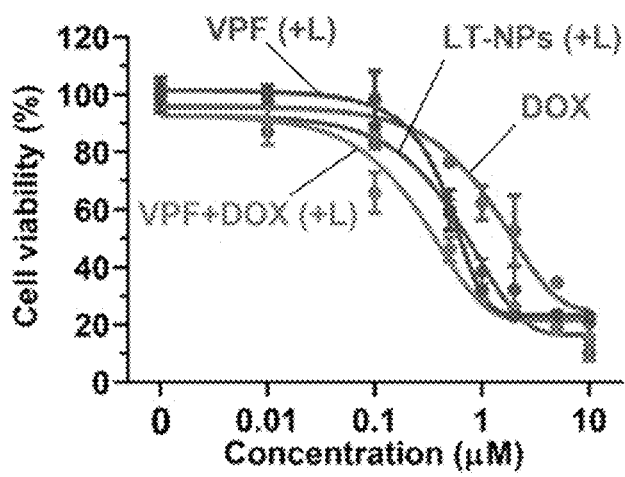
FIG. 4D shows the viabilities of CT26 cells after treatment with doxorubicin (DOX), verteporfin (VPF), a mixture of verteporfin and doxorubicin (VPF+DOX), and self-assembled nanoparticles (LT-NPs) and irradiation with visible light.

FIG. 4D shows the viabilities of CT26 cells after treatment with doxorubicin (DOX), verteporfin (VPF), a mixture of verteporfin and doxorubicin (VPF+DOX), and the self-assembled nanoparticles (LT-NPs) and irradiation with visible light.

Figure 4E:
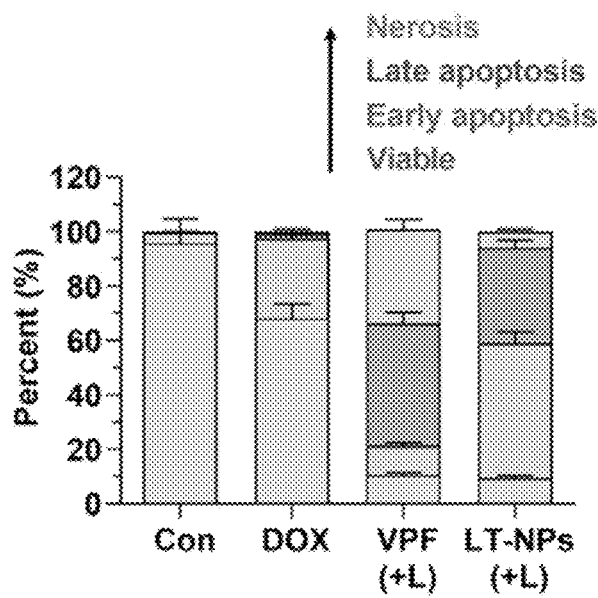
FIG. 4E shows the degrees of apoptosis in CT26 cells after treatment with doxorubicin (DOX), verteporfin (VPF), a mixture of verteporfin and doxorubicin (VPF+DOX), and self-assembled nanoparticles (LT-NPs), irradiation with visible light, and staining with Annexin-V and PI.

FIG. 4E shows the degrees of apoptosis in CT26 cells after treatment with doxorubicin (DOX), verteporfin (VPF), a mixture of verteporfin and doxorubicin (VPF+DOX), and the self-assembled nanoparticles (LT-NPs), irradiation with visible light, and staining with Annexin-V and PI.

As shown in FIGS. 4D and 4E, there were no significant differences between the viability of cells treated with the self-assembled nanoparticles (LT-NPs) and the viabilities of cells treated with the conventional drugs (doxorubicin and verteporfin). However, the degree of apoptosis caused by the self-assembled nanoparticles (LT-NPs) was significantly higher than that caused by the conventional drugs (doxorubicin and verteporfin).

Specifically, very little apoptosis was observed in the cells treated with doxorubicin (DOX) alone. The treatment with verteporfin (VPF) caused considerable apoptosis and necrosis but was found to increase the proportion of late apoptosis. In contrast, the treatment with the self-assembled nanoparticles caused significantly higher apoptosis and necrosis and led to lower proportions of late apoptosis and necrosis and a higher proportion of early apoptosis than any other treatment, demonstrating better anticancer activity of the self-assembled nanoparticles.

EXPERIMENTAL EXAMPLE 9

Evaluation of Immunogenic Cell Death by the Self-Assembled Nanoparticles (LT-NPs)

Immunogenic cell death (ICD) is a type of cell death triggered by certain anticancer drug families (including anthracycline-based anticancer drugs, oxaliplatin, and bortezomib). ICD allows dying/dead cancer cells acting as antigens to activate dendritic cells, resulting in the induction of antitumor immunity. ICD-induced cancer cells express ICD-specific markers, which are collectively referred to as damage-associated molecular patterns (DAMPs), on the cell surface or release them extracellularly. Representative examples of known ICD markers include calreticulin (CRT) expression on the cell surface, ATP release, and HMGB1 release.

The following experiment was conducted to determine whether antitumor immunity was induced by the self-assembled nanoparticles (LT-NPs) prepared in Example 1.

Samples

First, CT26 cells were plated in 35 mm cell culture dishes at a density of $1 \times 10^5$ cells/dish and doxorubicin (DOX) (5 μM), verteporfin (VPF) (5 μM) or the self-assembled nanoparticles (LT-NPs) (5 μM) were added to each dish. After 24-h culture, one half was exposed by irradiation with visible light using a 671 nm laser at 40 mW for 250 sec (+L) and the other half was not irradiated with visible light for comparison (−L). The immunogenic cell death of the self-assembled nanoparticles (LT-NPs) was evaluated using the cells and the cell culture media.

Calreticulin Analysis

Cells were stained with APC-conjugated CRT antibody for 12 h and observed with a confocal fluorescence microscope.

Analysis of Extracellular HSP70 and HMGB1 Expressions (Western Blotting)

Before staining the cells with APC-conjugated CRT antibody, culture media were separated from the cells and the extracellular expression levels of HMGB1 and HSP70 were analyzed by Western blotting.

Each cell culture medium was treated with RIPA buffer (Cell Signaling Technology) at 4° C. for 30 min and the protein amount of the lysate was analyzed using a Pierce BCA protein assay kit (Thermo Fisher Scientific) according to the manufacturer's protocol. After SDS-PAGE, proteins were transferred to a PVDF membrane (Bio-Rad), which was then treated with Tris-buffered saline (TBS-T) containing 5% skim milk and 0.1% Tween-20. The membrane was incubated with primary antibodies at 4° C. overnight. HSP70 and HMGB1 antibodies were used as the primary antibodies. The membrane was washed with TBS-T and incubated with a secondary antibody at room temperature for 1 h. The membrane was washed with TBS-T, treated with EZ-Western Lumi Pico or Femto reagent (DoGen), and analyzed using Fusion-Solo software (Vilber) according to the manufacturer's protocol to determine band intensities.

ATP Content

ATP was analyzed using a commercially available ATP assay kit (Beyotime Biotechnology) according to the manufacturer's protocol.

Statistics

Statistical analysis was done using one-way ANOVA test to determine significant differences in the mean value between groups. * indicates a significant difference at $p<0.05$,  indicates a significant difference at $p<0.01$, * indicates a significant difference at $p<0.001$, and N.S indicates no significant difference. Error bars indicate standard deviation.

Figure 4F:
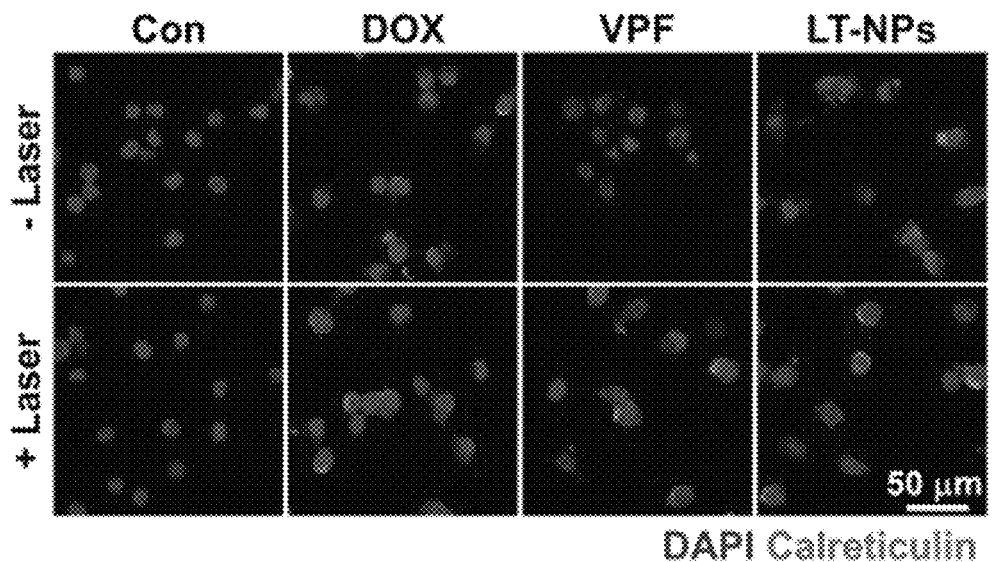
FIG. 4F shows the results of flow cytometry for CT26 cells after treatment with doxorubicin (DOX) (5 µM), verteporfin (VPF) (5 µM), and self-assembled nanoparticles (LT-NPs) (5 µM) and irradiation (+L) or non-irradiation with visible light (−L) to determine whether calreticulin (CRT) was expressed.
Figure 4G:
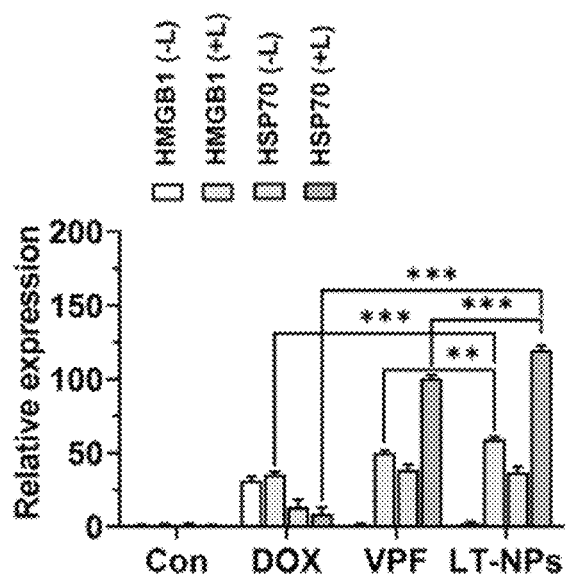
FIG. 4G shows the relative expression levels of HSP70 and HMGB1 released extracellularly from culture media of CT26 cells after treatment with doxorubicin (DOX) (5 µM), verteporfin (VPF) (5 µM), and self-assembled nanoparticles (LT-NPs) (5 µM) and irradiation (+L) or non-irradiation with visible light (−L), which were measured by Western blotting.
Figure 4H:
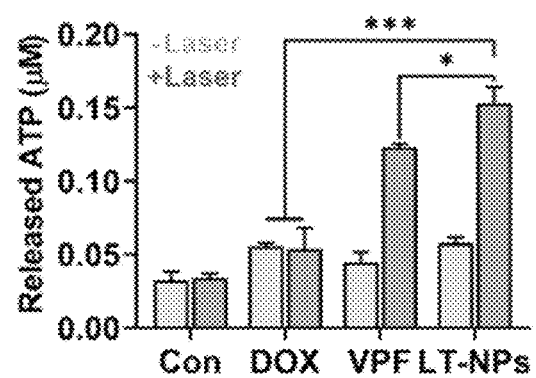
FIG. 4H shows the amounts of ATP released extracellularly from culture media of CT26 cells after treatment with doxorubicin (DOX) (5 µM), verteporfin (VPF) (5 µM), and self-assembled nanoparticles (LT-NPs) (5 µM) and irradiation (+L) or non-irradiation with visible light (−L), which were determined by quantitative analysis, FIG. 4I schematically shows an experimental procedure in Experimental Example 10.

FIG. 4F shows the results of flow cytometry for CT26 cells after treatment with doxorubicin (DOX) (5 μM), verteporfin (VPF) (5 μM), and the self-assembled nanoparticles (LT-NPs) (5 μM) and irradiation (+L) or non-irradiation with visible light (−L) to determine whether calreticulin (CRT) was expressed. FIG. 4G shows the relative expression levels of HSP70 and HMGB1 released extracellularly from culture media of CT26 cells after treatment with doxorubicin (DOX) (5 μM), verteporfin (VPF) (5 μM), and the self-assembled nanoparticles (LT-NPs) (5 μM) and irradiation (+L) or non-irradiation with visible light (−L), which were measured by Western blotting. FIG. 4H shows the amounts of ATP released extracellularly from culture media of CT26 cells after treatment with doxorubicin (DOX) (5 μM), verteporfin (VPF) (5 μM), and the self-assembled nanoparticles (LT-NPs) (5 μM) and irradiation (+L) or non-irradiation with visible light (−L), which were determined by quantitative analysis.

As shown in FIGS. 4F to 4H, the lowest calreticulin expression level as well as the lowest HMGB-1, HSP70 and ATP releases were observed when treated with doxorubicin alone.

In contrast, relatively increased calreticulin expression as well as relatively increased HMGB-1, HSP70, and ATP releases were observed when treated with verteporfin alone compared to when treated with doxorubicin alone.

Significantly higher calreticulin expression as well as significantly higher HMGB-1, HSP70, and ATP releases were observed when treated with the self-assembled nanoparticles (LT-NPs) than when treated with doxorubicin or verteporfin. These results concluded that the self-assembled nanoparticles (LT-NPs) significantly increase the release of DAMPs into cancer cells to induce more potent immunogenic cell death than the conventional anticancer drugs.

EXPERIMENTAL EXAMPLE 10

Activation of Immune Cells by the Self-Assembled Nanoparticles (LT-NPs)

Samples

Figure 4I:
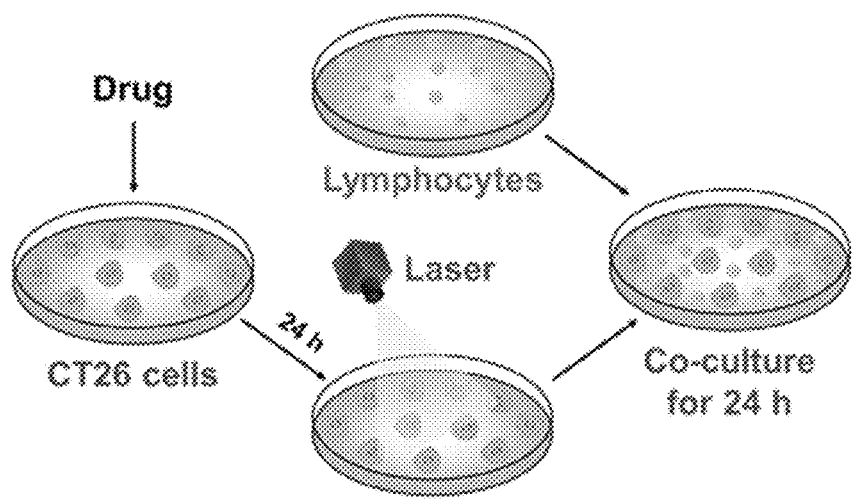
FIG. 4J shows the degrees of differentiation of CT26 cells into mature dendritic cells and activated T cells after treatment with doxorubicin (DOX) (5 µM), verteporfin (VPF) (5 µM), and self-assembled nanoparticles (LT-NPs) (5 µM), irradiation (+L) or non-irradiation with visible light (−L), and culture with spleen cells, which were analyzed by flow cytometry.

First, CT26 cells were plated in 100-pi cell culture dishes at a density of $1 \times 10^6$ cells/dish and cultured for stabilization for 24 h. Doxorubicin (DOX) (5 μM), verteporfin (VPF) (5 μ) or the self-assembled nanoparticles (LT-NPs) (5 μM) were added to each dish. After 24-h culture, one half was exposed by irradiation with visible light using a 671 nm laser at 40 mW for 250 sec (+L) and the other half was not irradiated with visible light for comparison (−L). $1 \times 10^6$ spleen cells isolated from Balb/c mice were added to each sample, followed by co-culture for 24 h (FIG. 4I).

Flow Cytometry

The degrees of differentiation into mature dendritic cells and activated T cells in each sample were analyzed using a flow cytometer.

Statistics

Statistical analysis was done using one-way ANOVA test to determine significant differences in the mean value between groups. * indicates a significant difference at $p<0.05$,  indicates a significant difference at $p<0.01$, * indicates a significant difference at $p<0.001$, and N.S indicates no significant difference. Error bars indicate standard deviation.

Figure 4J:
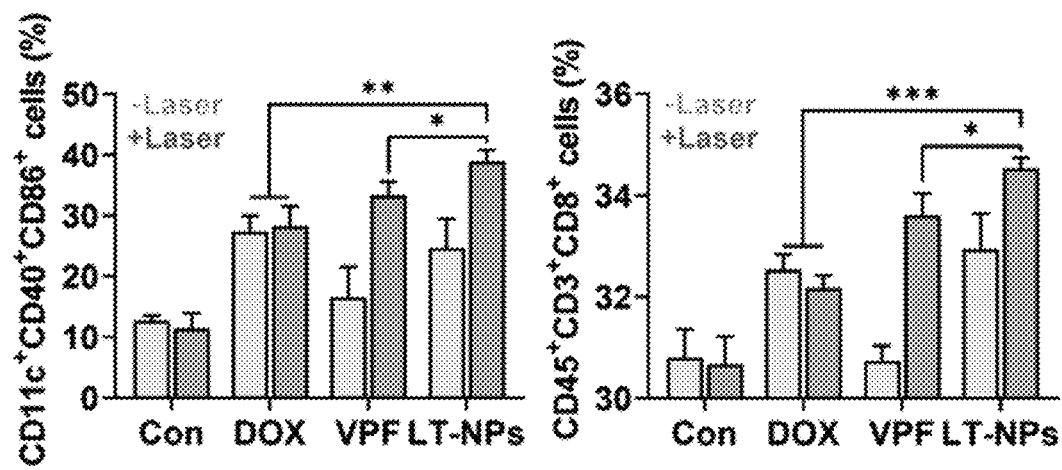

FIG. 4I schematically shows the experimental procedure in Experimental Example 10 and FIG. 4J shows the degrees of differentiation of CT26 cells into mature dendritic cells and activated T cells after treatment with doxorubicin (DOX) (5 μM), verteporfin (VPF) (5 μM), and the self-assembled nanoparticles (LT-NPs) (5 μM), irradiation (+L) or non-irradiation with visible light (−L), and culture with spleen cells, which were analyzed by flow cytometry.

As shown in FIG. 4J, the degrees of differentiation into mature dendritic cells and activated T cells were significantly higher when treated with the self-assembled nanoparticles (LT-NPs) than when treated with doxorubicin or verteporfin alone.

In conclusion, the inventive self-assembled nanoparticles (LT-NPs) induce more DAMPs than the conventional anticancer drugs, indicating that they significantly increase the activation of immune cells.

EXPERIMENTAL EXAMPLE 11

Evaluation of in vivo Behaviors of the Self-Assembled Nanoparticles (LT-NPs)

Experimental Animals

Thymic nude mice (6 weeks old, 20-25 g, male) bred in a sterile environment were used. The mice were acclimated for 2 weeks prior to starting the experiment. The mice had ad libitum access to food and water in cages maintained at a temperature of 22±2° C. and a humidity of 40-60% on a 12 h light and dark cycle during the experiment. All experimental procedures were performed according to the guidelines of the Institutional Animal Care and Use Committee of the Korea Institute of Science and Technology.

Sample Administration and Sampling

Colon cancer was induced in the male nude mice. To this end, $1\times10^6$ CT26 cells were subcutaneously inoculated into the left thigh of each mouse to construct a tumor animal model. Thereafter, the tumor was allowed to grow until its volume reached ~200-250 mm$^3$ prior to the experiment. For sample administration, the mice were randomly divided into 4 groups, 24 animals per group. Verteporfin (VPF) was intravenously administered at a concentration of 5 mg/kg ("VPF-administered group") and the self-assembled nanoparticles (LT-NPs) were intravenously administered at a concentration of 5 mg/kg ("LT-NPs-administered group").

The in vivo behaviors of the drugs in the administered groups were evaluated by near-infrared imaging using an IVIS Lumina system for 0.5-9 h.

Two Groups of Animal Models

Group 1 (VPF): Verteporfin (VPF) was intravenously administered at a concentration of 5 mg/kg Group 2 (LT-NPs): The self-assembled nanoparticles (LT-NPs) were intravenously administered at a concentration of 5 mg/kg Statistics Statistical analysis was done using one-way ANOVA test to determine significant differences in the mean value between groups. * indicates a significant difference at p<0.05,  indicates a significant difference at p<0.01, * indicates a significant difference at p<0.001, and N.S indicates no significant difference. Error bars indicate standard deviation.

Figure 5A:
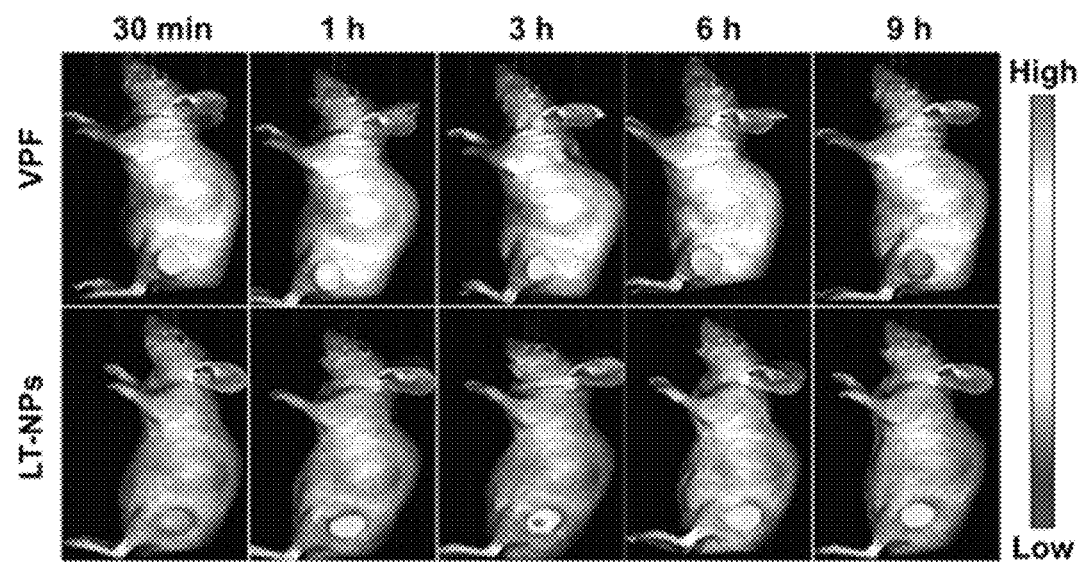
FIG. 5A shows the behaviors of a drug in animal models in Group 1 (VPF) and Group 2 (LT-NPs), which were analyzed by near-infrared imaging using an IVIS Lumina system.

FIG. 5A shows the behaviors of the drug in the animal models in Group 1 (VPF) and Group 2 (LT-NPs), which were analyzed by near-infrared imaging using an IVIS Lumina system. As shown in FIG. 5A, the fluorescence intensities of Group 2 treated with the self-assembled nanoparticles (LT-NPs) in cancer cells were higher than those of Group 1 treated with verteporfin. As a result, it was confirmed that the self-assembled nanoparticles (LT-NPs) accumulated in cancer cells with significantly higher efficacy than the conventional anticancer drug.

Figure 5B:
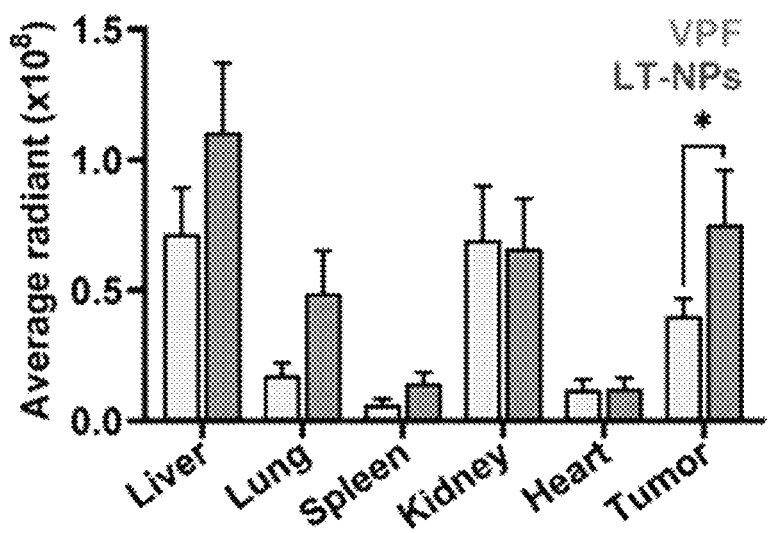
FIG. 5B shows the concentrations of a drug accumulated in tissues (liver, lung, spleen, kidney, heart, and tumor) of animal models in Group 1 (VPF) and Group 2 (LT-NPs)

FIG. 5B shows the concentrations of the drug accumulated in tissues (liver, lung, spleen, kidney, heart, and tumor) of the animal models in Group 1 (VPF) and Group 2 (LT-NPs). As shown in FIG. 5B, the fluorescence intensities of Group 2 treated with the self-assembled nanoparticles (LT-NPs) in cancer cells were higher than those of Group 1 treated with verteporfin. As a result, it was confirmed again that the self-assembled nanoparticles (LT-NPs) accumulated in cancer cells with significantly higher efficacy than the conventional anticancer drug.

Figure 5C:
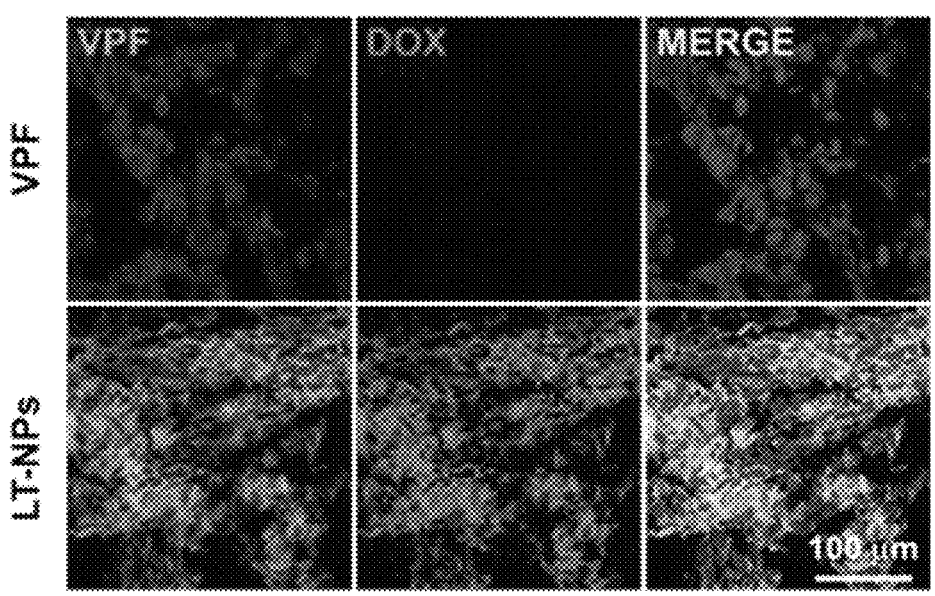
FIG. 5C shows the results of histological analysis for cancer cells in animal models in Group 1 (VPF) and Group 2 (LT-NPs)

FIG. 5C shows the results of histological analysis for cancer cells in the animal models in Group 1 (VPF) and Group 2 (LT-NPs). FIG. 5C again confirmed that the self-assembled nanoparticles (LT-NPs) accumulated in cancer cells with significantly higher efficacy than the conventional anticancer drug.

EXPERIMENTAL EXAMPLE 12

Anticancer Effect of the Self-Assembled Nanoparticles (LT-NPs)

Experimental Animals

Thymic nude mice (6 weeks old, 20-25 g, male) bred in a sterile environment were used. The mice were acclimated for 2 weeks prior to starting the experiment. The mice had ad libitum access to food and water in cages maintained at a temperature of 22±2° C. and a humidity of 40-60% on a 12 h light and dark cycle during the experiment. All experimental procedures were performed according to the guidelines of the Institutional Animal Care and Use Committee of the Korea Institute of Science and Technology.

Sample Administration and Sampling

Colon cancer was induced in the male nude mice. To this end, $1\times10^6$ CT26 cells were subcutaneously inoculated into the left thigh of each mouse to construct a tumor animal model. Thereafter, the tumor was allowed to grow until its volume reached ~200-250 mm$^3$ prior to the experiment. For sample administration, the mice were randomly divided into 4 groups, 24 animals per group. In a control ("Con"), animals were administered intravenously PBS at a concentration of 5 mg/kg twice on days 0 and 2. In a DOX-administered group, animals were administered intravenously doxorubicin (DOX) at a concentration of 5 mg/kg twice on days 0 and 2. In a VPF(+L)-administered group, animals were administered intravenously verteporfin (VPF) at a concentration of 5 mg/kg twice on days 0 and 2 and exposed by irradiation with visible light using a 671 nm laser at 40 mW for 250 sec. In an LT-NPs(-L)-administered group, animals were administered intravenously the self-assembled nanoparticles (LT-NPs) at a concentration of 5 mg/kg twice on days 0 and 2. In an LT-NPs(+L)-administered group, animals were administered intravenously the self-assembled nanoparticles (LT-NPs) at a concentration of 5 mg/kg twice on days 0 and 2 and exposed by irradiation with visible light using a 671 nm laser at 40 mW for 250 sec.

Changes in tumor volume (maximum diameter x minimum diameter$^2$x0.53) in the groups were measured every 2 days for a total of 0-25 days. After 7 days, blood was harvested from each group and analyzed for HSP70, HMGB1, immunogenic apoptotic cancer cells, mature dendritic cells, activated T cells, and IFN-γ levels.

Five Groups of Animal Models

Group 1 (Con): PBS was administered intravenously at a concentration of 5 mg/kg twice on days 0 and 2.

Group 2 (DOX): Doxorubicin (DOX) was administered intravenously at a concentration of 5 mg/kg twice on days 0 and 2.

Group 3 (VPF(+L)): Verteporfin (VPF) was administered intravenously at a concentration of 5 mg/kg twice on days 0 and 2, followed by irradiation with visible light using a 671 nm laser at 40 mW for 250 sec.

Group 4 (LT-NPs(-L)): The self-assembled nanoparticles (LT-NPs) were administered intravenously at a concentration of 5 mg/kg twice on days 0 and 2.

Group 5 (LT-NPs(+L)): The self-assembled nanoparticles (LT-NPs) were administered intravenously at a concentration of 5 mg/kg twice on days 0 and 2, followed by irradiation with visible light using a 671 nm laser at 40 mW for 250 sec.

Histological Analysis 9 h after drug administration, cancer tissues were excised from each group. Each cancer tissue was sectioned to a thickness of 10 μm, washed twice with DBPS, and stained with DAPI in the dark for 15 min. The section was imaged using a Leica TCS SP8 focal microscope (Leica Microsystems GmbH).

Analysis of Immune Cells

Immune cells infiltrated into cancer cells in each group were analyzed. After 7 days, animals in each group were euthanized under anesthesia and cancer tissues were collected. Monocytes were isolated using a tumor dissociation kit (Miltenyi Biotec) according to the manufacturer's protocol. Next, the monocytes were incubated with Fc block for 5 min to avoid non-specific binding and stained with antibodies for 1 h to determine the proportions of i) immunogenic apoptotic cancer cells (CD45 and CRT staining), ii) activated T cells (CD45, CD3, and CD8 staining), and iii) mature dendritic cells (CD11c, CD40, and CD86 staining) in the cancer tissues.

Statistics

Statistical analysis was done using one-way ANOVA test to determine significant differences in the mean value between groups. * indicates a significant difference at p<0.05,  indicates a significant difference at p<0.01, * indicates a significant difference at p<0.001, and N.S indicates no significant difference. Error bars indicate standard deviation.

Figure 5D:
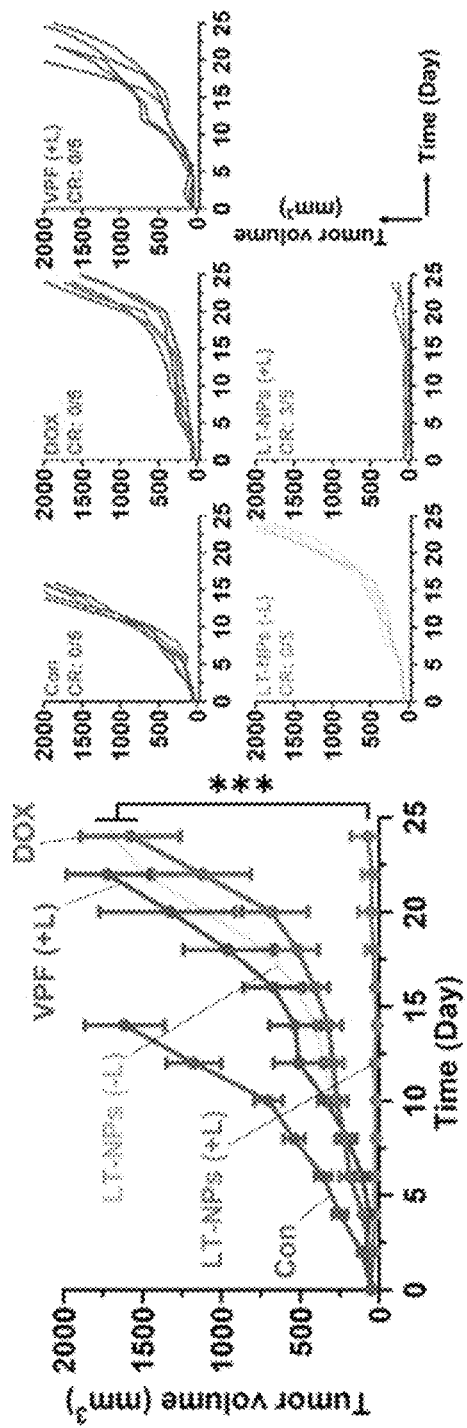
FIG. 5D shows changes in tumor volume in animal models in Groups 1-5.

FIG. 5D shows changes in tumor volume in the animal models in Groups 1-5. As shown in FIG. 5D, the growth of cancer cells was significantly reduced in the group co-treated with the self-assembled nanoparticles (LT-NPs) and the laser compared to in the groups administered with other anticancer drugs. 3 out of the animal models in Group 5 (LT-NPs(+L)) were cured. All animal models in Groups 2-4 experienced tumor growth and died within 25 days, and none of them were cured.

Figure 5E:
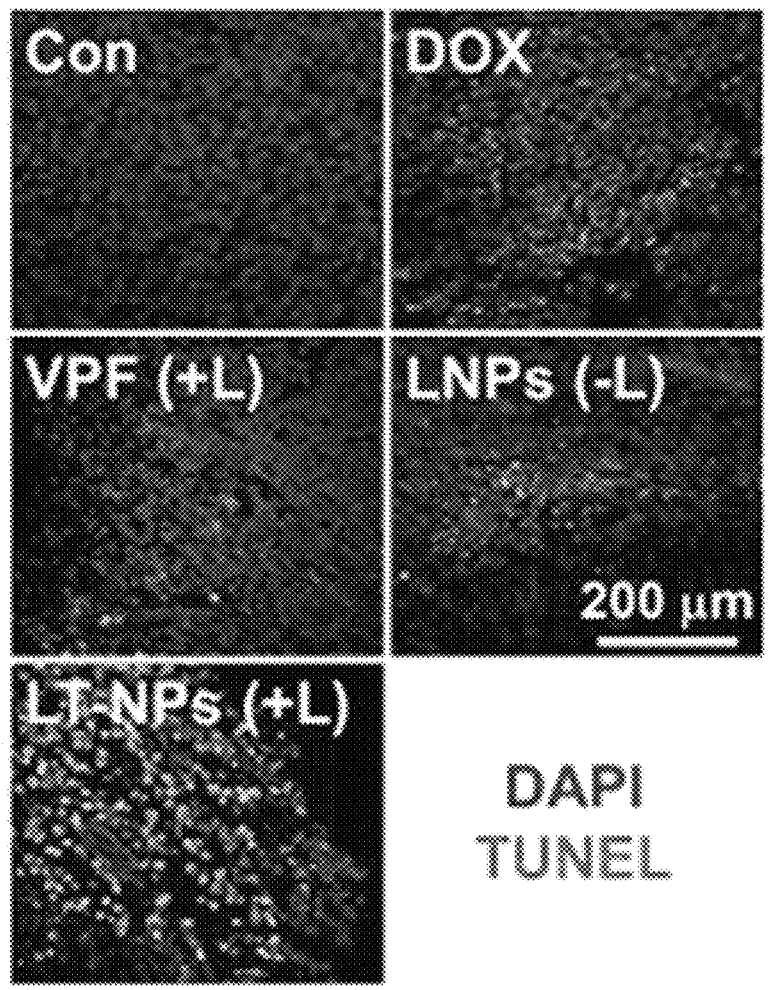
FIG. 5E shows images revealing the degrees of apoptosis in cancer cells in animal models in Groups 1-5 after 7 days.

FIG. 5E shows images revealing the degrees of apoptosis in cancer cells in the animal models in Groups 1-5 after 7 days. As shown in FIG. 5E, the degree of apoptosis in cancer cells was significantly high in the group co-treated with the self-assembled nanoparticles (LT-NPs) and the laser compared to those in the other groups.

Figure 5F:
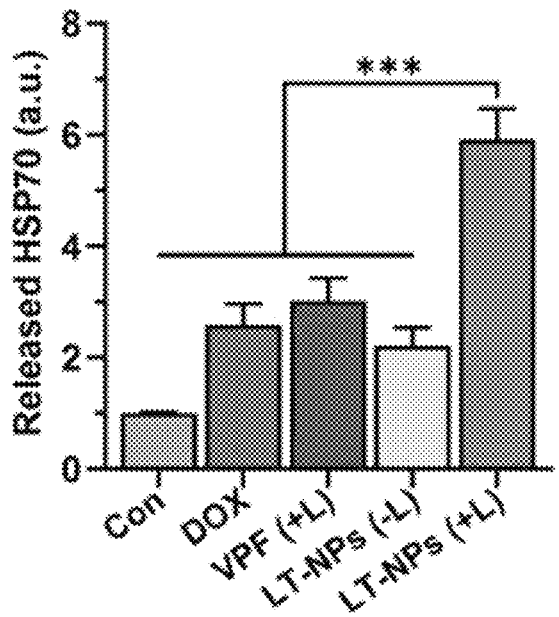
FIGS. 5F to 5K show the amounts of HSP70 (f), the amounts of HMGB1 (g), the proportions of immunogenic apoptotic cancer cells (h), the proportions of mature dendritic cells (i), the proportions of activated T cells (j), and the expression levels of IFN-γ in cancer tissues in animal models in Groups 1-5 after 7 days.
Figure 5G:
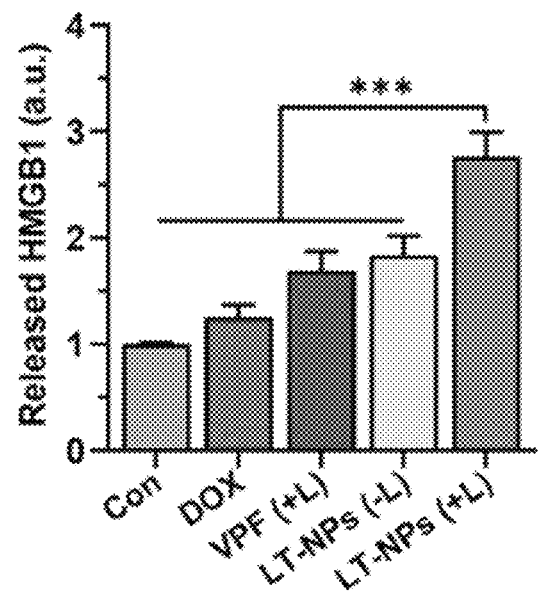
Figure 5H:
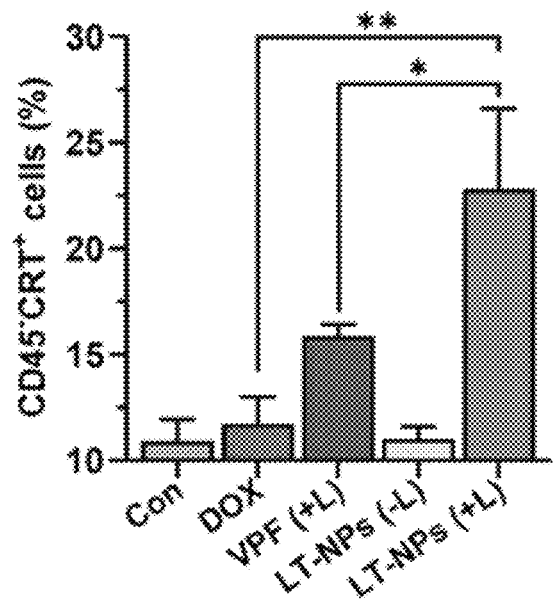
Figure 5I:
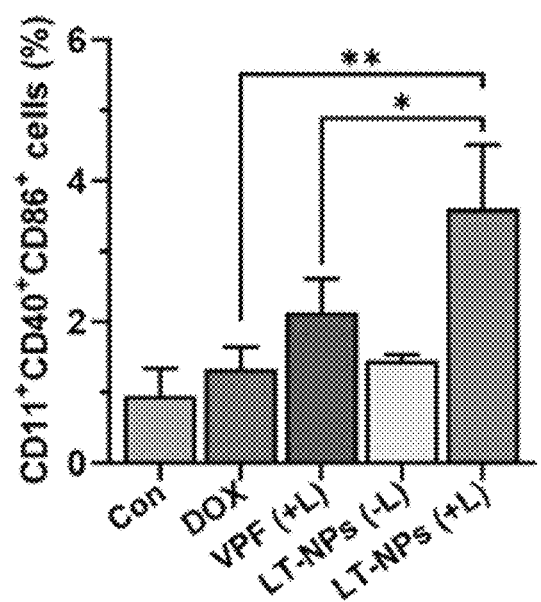
Figure 5J:
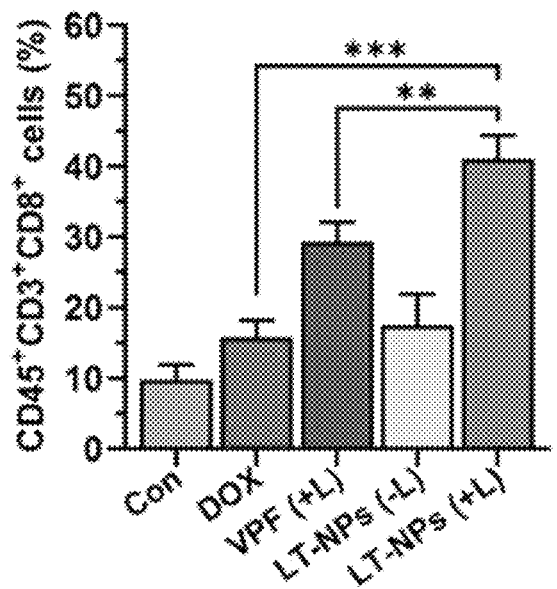
Figure 5K:
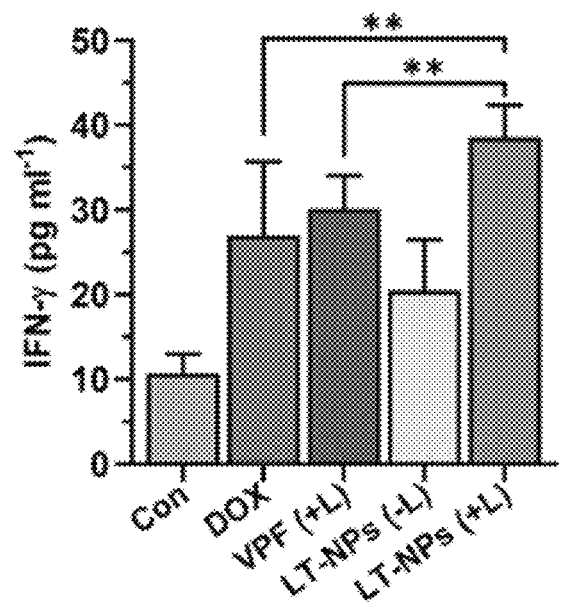

FIGS. 5F and 5G show the expression levels of HSP70 (f) and HMGB1 (g) in the animal models in Groups 1-5 after 7 days, which were analyzed by Western blotting. As shown in FIGS. 5F and 5G, the expression levels of HSP70 and HMGB1 were significantly high in the group co-treated with the self-assembled nanoparticles (LT-NPs) and the laser compared to those in the other groups, demonstrating that the self-assembled nanoparticles (LT-NPs) induce potent immunogenic cell death in tumors to generate DAMPs.

FIGS. 5H to 5K show the proportions of immunogenic apoptotic cancer cells (h), the proportions of mature dendritic cells (i), the proportions of activated T cells (j), and the expression levels of IFN-γ in cancer tissues in the animal models in Groups 1-5 after 7 days.

As shown in FIGS. 5h to 5k, the proportions of immunogenic apoptotic cancer cells, mature dendritic cells, and activated T cells in the group administered the self-assembled nanoparticles (LT-NPs) and treated with the laser were significantly higher than those in the other groups. These results demonstrate that the self-assembled nanoparticles (LT-NPs) induce potent immunogenic cell death in tumors to generate DAMPs, leading to significant induction of infiltration and activity of immune cells.

EXPERIMENTAL EXAMPLE 13

Combined Administration of the Self-Assembled Nanoparticles (LT-NPs) and Immune Checkpoint Inhibitor Experimental Animals Thymic nude mice (6 weeks old, 20-25 g, male) bred in a sterile environment were used. The mice were acclimated for 2 weeks prior to starting the experiment. The mice had ad libitum access to food and water in cages maintained at a temperature of 22±2° C. and a humidity of 40-60% on a 12 h light and dark cycle during the experiment. All experimental procedures were performed according to the guidelines of the Institutional Animal Care and Use Committee of the Korea Institute of Science and Technology.

Sample Administration and Sampling

Colon cancer was induced in the male nude mice. To this end, $1 \times 10^6$ CT26 cells were subcutaneously inoculated into the left thigh of each mouse to construct a tumor animal model.

Thereafter, the tumor was allowed to grow until its volume reached ~200-250 mm³ prior to the experiment. For sample administration, the mice were randomly divided into 5 groups, 5 animals per group. In a control ("Con"), animals were administered intravenously PBS at a concentration of 5 mg/kg twice on days 0 and 2. In a PD-L1 Ab-administered group, animals were administered intraperitoneally PD-L1 Ab (Bioxbio) at a concentration of 10 mg/kg twice on days 0 and 2. In a DOX+PD-L1 Ab-administered group, animals were administered intravenously doxorubicin (DOX) at a concentration of 5 mg/kg and intraperitoneally PD-L1 Ab at a concentration of 10 mg/kg twice on days 0 and 2. In a VPF+PD-L1 Ab(+L)-administered group, animals were administered intravenously verteporfin (VPF) at a concentration of 5 mg/kg and intraperitoneally PD-L1 Ab at a concentration of 10 mg/kg twice on days 0 and 2 and exposed by irradiation with visible light using a 671 nm laser at 40 mW for 250 sec. In an LT-NPs+PD-L1 AB(+L)-administered group, animals were administered intravenously the self-assembled nanoparticles (LT-NPs) at a concentration of 5 mg/kg and intraperitoneally PD-L1Ab at a concentration of 10 mg/kg twice on days 0 and 2 and exposed by irradiation with visible light using a 671 nm laser at 40 mW for 250 sec.

Changes in tumor volume (maximum diameter×minimum diameter²×0.53) in the groups were measured every 2 days for a total of 0-100 days.

Five Groups of Animal Models

Group 1 (Con): PBS was administered intravenously at a concentration of 5 mg/kg twice on days 0 and 2.

Group 2 (PD-L1 Ab): PD-L1 Ab was administered intravenously at a concentration of 10 mg/kg twice on days 0 and 2.

Group 3 (DOX+PD-L1 Ab): Doxorubicin (DOX) at a concentration of 5 mg/kg and PD-L1 Ab at a concentration of 10 mg/kg were administered simultaneously twice on days 0 and 2.

Group 4 (VPF+PD-L1 Ab(+L)): Verteporfin (VPF) at a concentration of 5 mg/kg and PD-L1 Ab at a concentration of 10 mg/kg were administered simultaneously twice on days 0 and 2, followed by irradiation with visible light using a 671 nm laser at 40 mW for 250 sec.

Group 5 (LT-NPs+PD-L1 Ab(+L)): The self-assembled nanoparticles (LT-NPs) at a concentration of 5 mg/kg and PD-L1 Ab at a concentration of 10 mg/kg were administered simultaneously twice on days 0 and 2, followed by irradiation with visible light using a 671 nm laser at 40 mW for 250 sec.

Histological Analysis 9 h after drug administration, cancer tissues were excised from each group. Each cancer tissue was sectioned to a thickness of 10 μm, washed twice with DBPS, and stained with DAPI in the dark for 15 min. The section was imaged using a Leica TCS SP8 focal microscope (Leica Microsystems GmbH).

Statistics

Statistical analysis was done using one-way ANOVA test to determine significant differences in the mean value between groups. * indicates a significant difference at $p<0.05$,  indicates a significant difference at $p<0.01$, * indicates a significant difference at $p<0.001$, and N.S indicates no significant difference. Error bars indicate standard deviation. "CR" indicates the number of animals who have recovered from cancer completely.

Figure 6A:
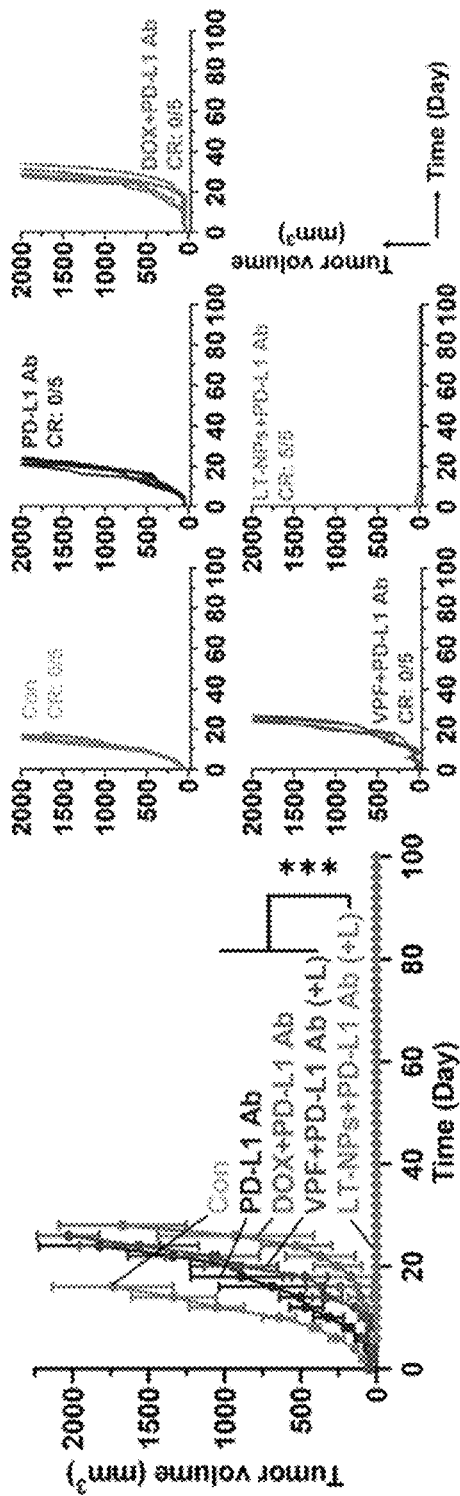
FIG. 6A shows changes in tumor volume (maximum diameter×minimum diameter$^2$×0.53) in animal models in Groups 1-5.

FIG. 6A shows changes in tumor volume (maximum diameter×minimum diameter$^2$×0.53) in the animal models in Groups 1-5. As shown in FIG. 6A, the tumor volume was significantly reduced in Group 5 (LT-NPs+PD-L1 Ab(+L)) co-administered the self-assembled nanoparticles (LT-NPs) and PD-L1 Ab than those in the other groups. Particularly, all animals in the groups administered the conventional anticancer drugs singly or simultaneously were not cured and died. In contrast, all animals in Group 5 (LT-NPs+PD-L1 Ab(+L)) co-administered the self-assembled nanoparticles (LT-NPs) and PD-L1 Ab were completely cured.

Figure 6B:
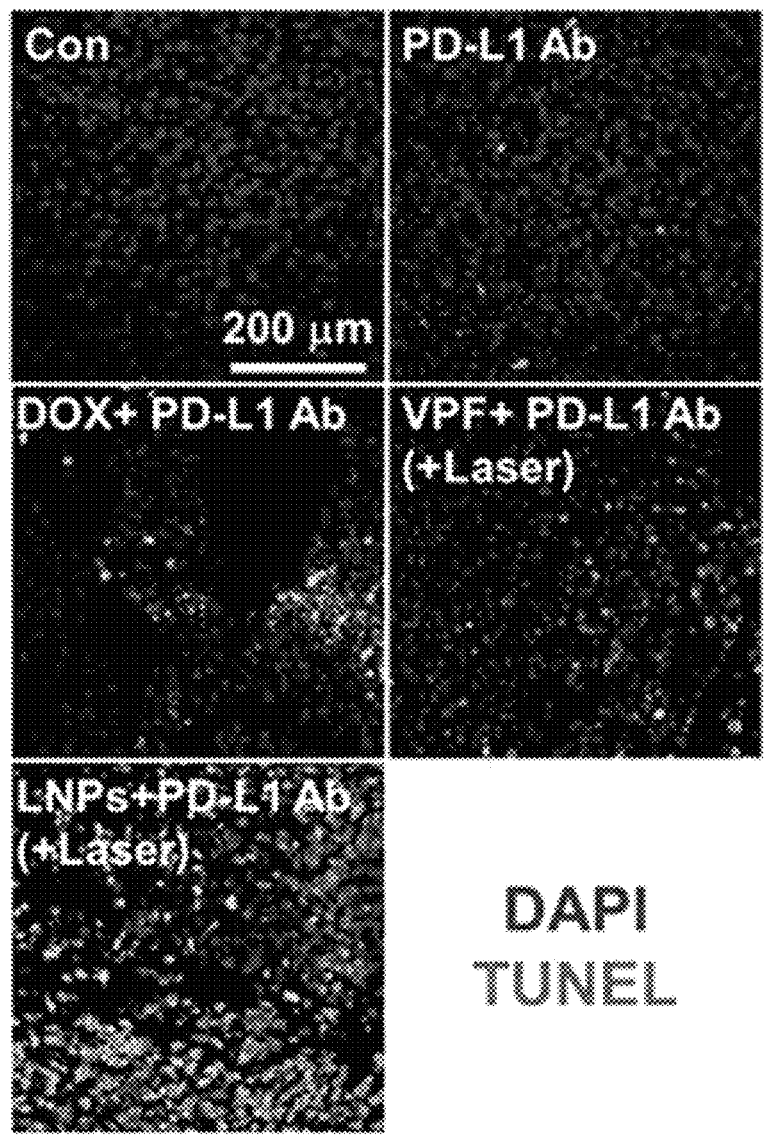
FIG. 6B shows images revealing the degrees of apoptosis in cancer cells in animal models in Groups 1-5 after 7 days.

FIG. 6B shows images revealing the degrees of apoptosis in cancer cells in the animal models in Groups 1-5 after 7 days. As shown in FIG. 6B, the degree of apoptosis in cancer cells was significantly higher than in Group 5 (LT-NPs+PD-L1 Ab(+L)) co-administered the self-assembled nanoparticles (LT-NPs) and PD-L1 Ab than those in the other groups. Particularly, the effects of co-administration of the conventional anticancer drugs and the immune checkpoint inhibitor were negligible. In contrast, the co-administration of the inventive self-assembled nanoparticles (LT-NPs) and the immune checkpoint inhibitor was almost completely effective in treating cancer. This effect can be considered to be beyond significant and unpredictable.

Figure 6C:
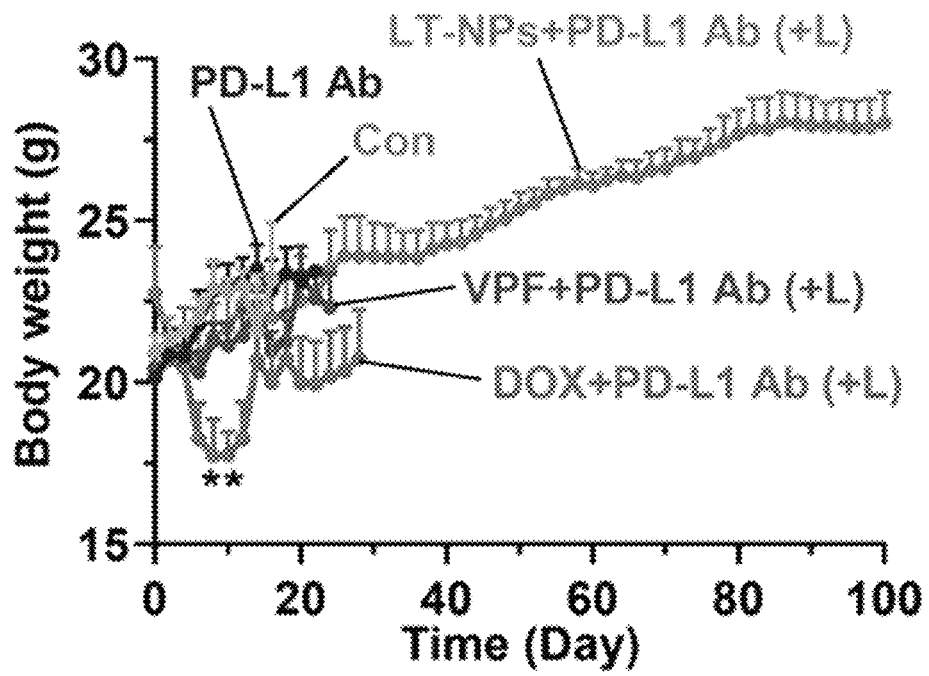
FIG. 6C shows changes in the body weight of animal models in Groups 1-5.
Figure 6D:
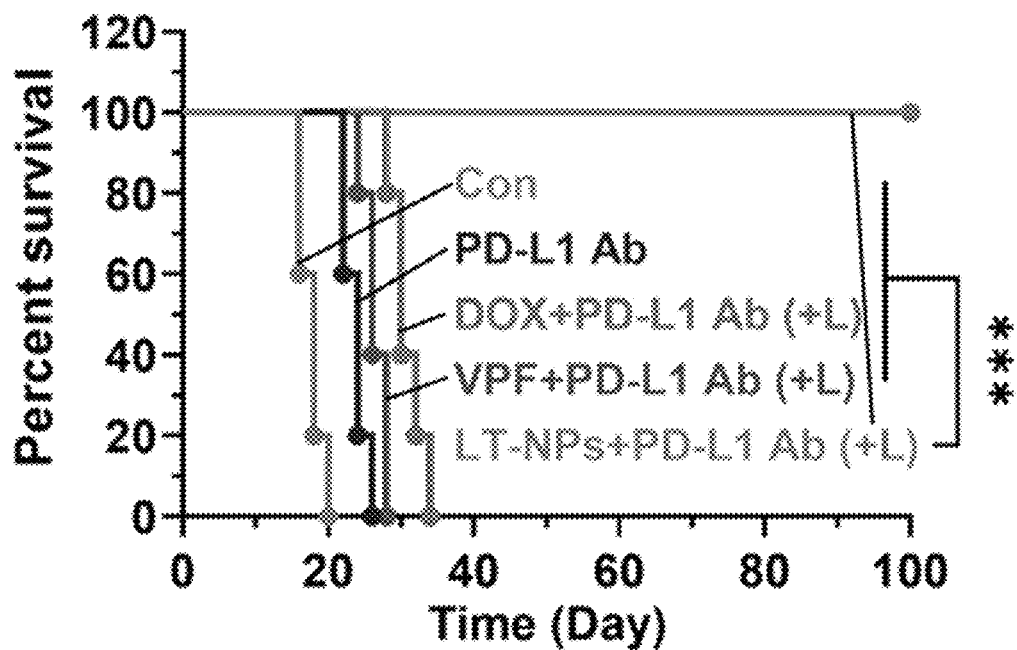
FIG. 6D shows the survival rates (%) of animal models in Groups 1-5.

FIG. 6C shows changes in the body weight of the animal models in Groups 1-5 and FIG. 6D shows the survival rates (%) of the animal models in Groups 1-5.

As shown in FIGS. 6C and 6D, the body weight and survival rate (%) of the animals in Group 5 (LT-NPs+PD-L1 Ab(+L)) co-administered the self-assembled nanoparticles (LT-NPs) and PD-L1 Ab were significantly increased compared to those in the other groups. The animals in the groups administered the conventional anticancer drugs lost their body weight and died within 40 days.

EXPERIMENTAL EXAMPLE 14

Evaluation of Inhibitory Efficacy of the Self-Assembled Nanoparticles (LT-NPs) on Cancer Recurrence Experimental Animals Thymic nude mice (6 weeks old, 20-25 g, male) bred in a sterile environment were used. The mice were acclimated for 2 weeks prior to starting the experiment. The mice had ad libitum access to food and water in cages maintained at a temperature of 22±2° C. and a humidity of 40-60% on a 12 h light and dark cycle during the experiment. All experimental procedures were performed according to the guidelines of the Institutional Animal Care and Use Committee of the Korea Institute of Science and Technology.

Cancer Recurrence Models—In vivo Immune Memory

Colon cancer was induced in the male nude mice. To this end, $1\times10^6$ CT26 cells were subcutaneously inoculated into the left thigh of each mouse to construct a tumor animal model. Thereafter, the tumor was allowed to grow until its volume reached ~200-250 mm$^3$ prior to the experiment. The animals were administered intravenously the self-assembled nanoparticles (LT-NPs) at a concentration of 5 mg/kg and intraperitoneally PD-L1 Ab at a concentration of 10 mg/kg on days 0 and 2 and exposed by irradiation with visible light using a 671 nm laser at 40 mW for 250 sec. The animals were bred for 100 days to recover from cancer.

In vivo immune memory in the cured mice was confirmed. To this end, $1\times10^6$ CT26 cells were subcutaneously inoculated into the same site of each mouse as the site inoculated with the cancer cells to construct a cancer recurrence model (CR). Changes in tumor volume (maximum diameter×minimum diameter$^2$×0.53) were measured.

Cancer cells were inoculated into untreated male nude mice to construct cancer animal models (control (naive)).

Two Groups of Animal Models

Group 1 (Naive): Cancer cells were inoculated into untreated male nude mice.

Group 2 (CR): Cancer animal models were administered intravenously the self-assembled nanoparticles (LT-NPs) at a concentration of 5 mg/kg and intraperitoneally PD-L1 Ab at a concentration of 10 mg/kg on days 0 and 2 and irradiated with visible light using a 671 nm laser at 40 mW for 250 sec to recover from cancer. After 100 days, cancer cells were inoculated into the same site for cancer recurrence.

Analysis of Immune Cells

Immune cells infiltrated into cancer cells in each group were analyzed. After 100 days, animals in each group were euthanized under anesthesia and cancer tissues were collected. Monocytes were isolated using a tumor dissociation kit (Miltenyi Biotec) according to the manufacturer's protocol. Next, the monocytes were incubated with Fc block for 5 min to avoid non-specific binding and stained with antibodies for 1 h to determine the proportions of activated T cells (CD3, CD8, CD44, and CD62 multi-staining) in the cancer tissues.

Figure 6E:
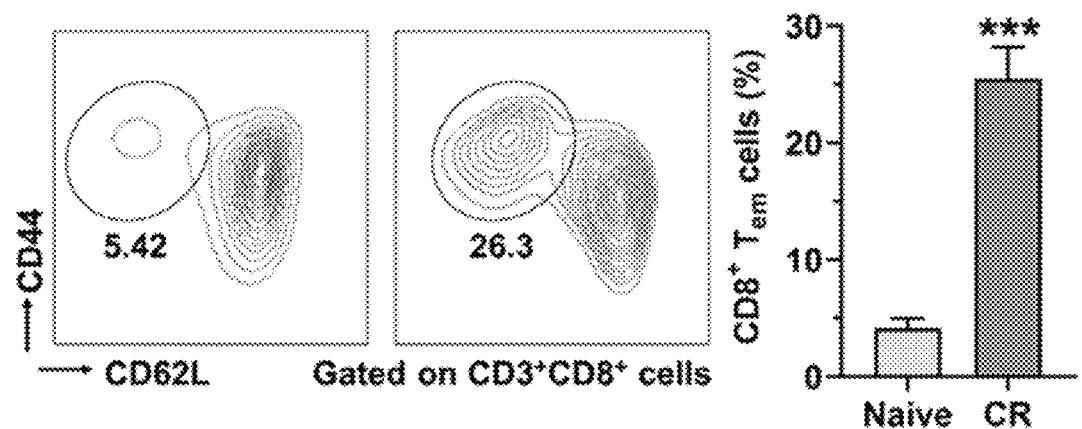
FIG. 6E shows the proportions of activated T cells (CD45, CD3, and CD8) in cancer cells in animal models in Groups 1 and 2 on day 20 after second inoculation with cancer cells.

FIG. 6E shows the proportions of activated T cells (CD45, CD3, and CD8) in cancer cells in the animal models in Groups 1 and 2 on day 20 after second inoculation with cancer cells.

As shown in FIG. 6E, in Group 2 (CR) where the self-assembled nanoparticles (LT-NPs) and PD-L1 Ab were administered and visible light was irradiated to recover from cancer, a large number of memory T cells (corresponding to 5 times that in Group 1 (Naive)) were present in the spleen tissues even when cancer cells were re-inoculated. In contrast, memory T cells were present at a very low concentration in Group 1 (Naive).

Figure 6F:
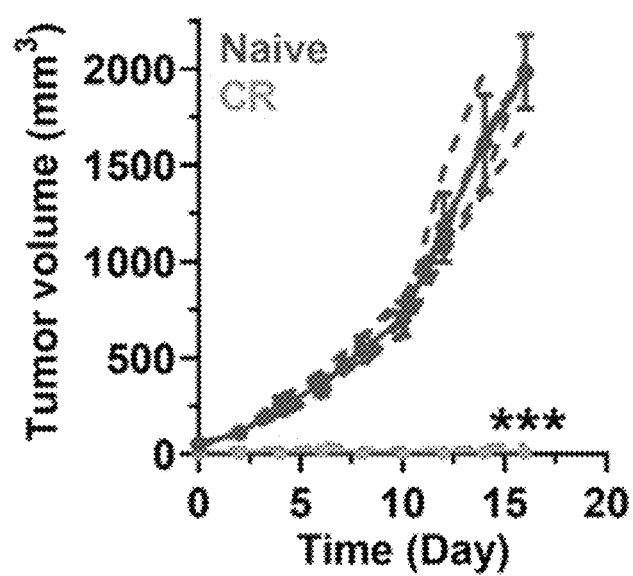
FIG. 6F shows changes in tumor volume in animal models in Groups 1 and 2 for 20 days after second inoculation with cancer cells.

FIG. 6F shows changes in tumor volume in the animal models in Groups 1 and 2 for 20 days after second inoculation with cancer cells.

As shown in FIG. 6F, cancer growth was significantly suppressed in Group 2 (CR) where the self-assembled nanoparticles (LT-NPs) and PD-L1 Ab were administered and visible light was irradiated to recover from cancer, compared to in the naive group. These results concluded that the self-assembled nanoparticles (LT-NPs) can establish cancer-specific immune memory in vivo to prevent further cancer recurrence.

Figure 6G:
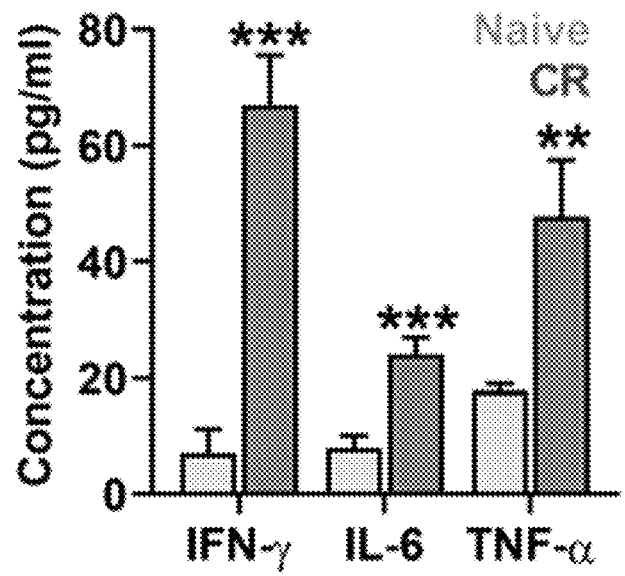
FIG. 6G shows the expression levels of various cytokines in the blood of animal models in Groups 1 and 2 on day 20 after second inoculation with cancer cells.

FIG. 6G shows the expression levels of various cytokines in the blood of the animal models in Groups 1 and 2 on day 20 after second inoculation with cancer cells. As shown in FIG. 6G, the expression levels of cytokines in Group 2 (CR) where the self-assembled nanoparticles (LT-NPs) and PD-L1 Ab were administered and visible light was irradiated to recover from cancer were significantly increased compared to those in the naive group. These results concluded that the administration of the self-assembled nanoparticles (LT-NPs) remarkably maximizes the efficacy of the immune checkpoint inhibitor to cure tumor and is effective in preventing further cancer recurrence.

EXPERIMENTAL EXAMPLE 15

Evaluation of Inhibitory Efficacy of Co-Administration of the Self-Assembled Nanoparticles (LT-NPs) and Immune Checkpoint Inhibitor on Cancer Metastasis Experimental Animals Thymic nude mice (6 weeks old, 20-25 g, male) bred in a sterile environment were used. The mice were acclimated for 2 weeks prior to starting the experiment. The mice had ad libitum access to food and water in cages maintained at a temperature of 22±2° C. and a humidity of 40-60% on a 12 h light and dark cycle during the experiment. All experimental procedures were performed according to the guidelines of the Institutional Animal Care and Use Committee of the Korea Institute of Science and Technology.

Cancer Metastasis Models

Colon cancer was induced in the male nude mice. To this end, $1 \times 10^6$ CT26 cells were subcutaneously inoculated into the left thigh of each mouse to construct a tumor animal model. After 7 days, samples were administered as follows. In a control ("Con"), animals were administered intravenously PBS at a concentration of 5 mg/kg twice on days 0 and 2. In a PD-L1 Ab-administered group, animals were administered intraperitoneally PD-L1 Ab at a concentration of 10 mg/kg twice on days 0 and 2. In a VPF+PD-L1 Ab-administered group, animals were administered intravenously verteporfin (VPF) at a concentration of 5 mg/kg and intraperitoneally PD-L1 Ab at a concentration of 10 mg/kg on days 0 and 2 and, after 6 h, exposed by irradiation with visible light using a 671 nm laser at 100 mW for 15 min. In an LT-NPs+PD-L1 Ab(+L)-administered group, animals were administered intravenously the self-assembled nanoparticles (LT-NPs) at a concentration of 5 mg/kg and intraperitoneally PD-L1 Ab at a concentration of 10 mg/kg on days 0 and 2 and, after 6 h, exposed by irradiation with visible light using a 671 nm laser at 100 mW for 15 min.

After 24 h, $1 \times 10^5$ CT26 cells were further injected into the groups via the tail vein to induce lung metastasis. 20 days after induction of lung metastasis, the lung tissues was excised, followed by H&E and immunohistological staining.

Four Groups of Animal Models

Group 1 (Con): PBS was administered at a concentration of 5 mg/kg twice on days 0 and 2. After 24 h, CT26 cells were administered via the tail vein.

Group 2 (PD-L1 Ab): PD-L1 Ab was administered at a concentration of 10 mg/kg twice on days 0 and 2. After 24 h, CT26 cells were administered via the tail vein.

Group 3 (VPF+PD-L1 Ab(+L)): Verteporfin (VPF) at a concentration of 5 mg/kg and PD-L1 Ab at a concentration of 10 mg/kg were administered simultaneously twice on days 0 and 2, followed by irradiation with visible light using a 671 nm laser at 40 mW for 250 sec. After 24 h, CT26 cells were administered via the tail vein.

Group 4 (LT-NPs+PD-L1 Ab(+L)): The self-assembled nanoparticles (LT-NPs) at a concentration of 5 mg/kg and PD-L1 Ab at a concentration of 10 mg/kg were administered simultaneously twice on days 0 and 2, followed by irradiation with visible light using a 671 nm laser at 40 mW for 250 sec. After 24 h, CT26 cells were administered via the tail vein.

Immunohistological Staining

For immunohistological staining, metastatic cancer tissues (lung tissues) were harvested from the animal models in Groups 1-4 and were fixed in 10% neutral buffered formalin. Then, each fixed tissue was embedded in paraffin and sectioned to a size of 4 μm. The section was dried at 56° C. for 1 h. The section was deparaffinized for staining, rehydrated with EZprep, and washed with reaction buffer (Ventana Medical Systems). Thereafter, Ki67 and CD8+ antibodies were heated in Tri-EDTA buffer at 90° C. for 30 min. After removal of the antibodies, the tissue was observed with a microscope.

Statistics

Statistical analysis was done using one-way ANOVA test to determine significant differences in the mean value between groups. * indicates a significant difference at $p<0.05$,  indicates a significant difference at $p<0.01$, * indicates a significant difference at $p<0.001$, and N.S indicates no significant difference. Error bars indicate standard deviation.

Figure 7A:
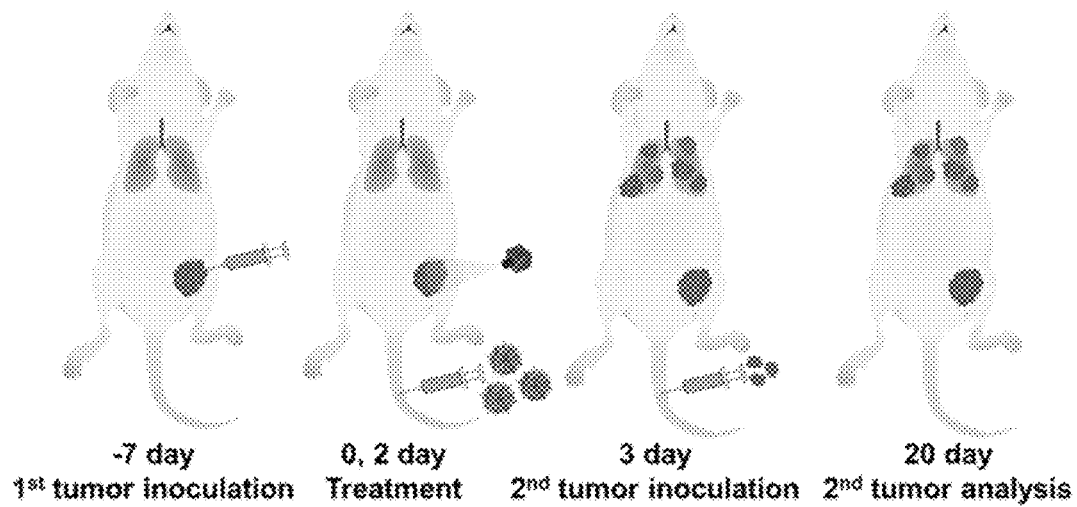
FIG. 7A schematically shows an experimental design in Experimental Example 15.
Figure 7B:
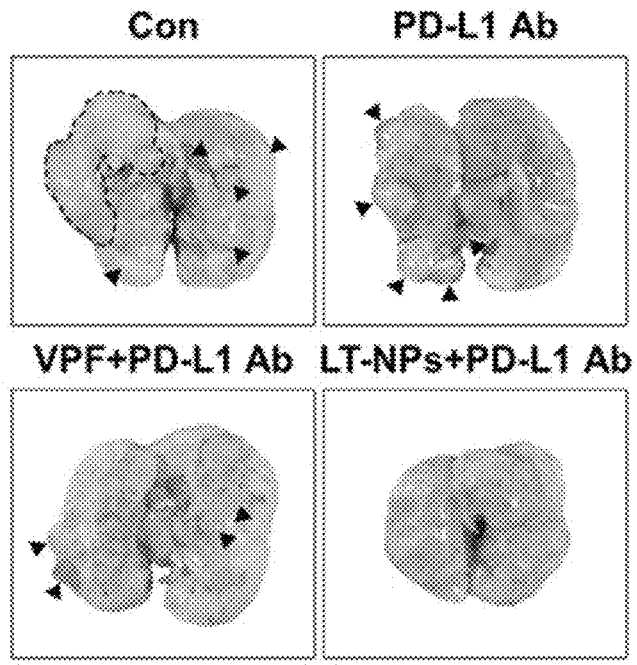
FIG. 7B shows images of lung tissues of animal models in Groups 1-4 on day 20 after induction of lung metastasis.

FIG. 7A schematically shows an experimental design in Experimental Example 15 and FIG. 7B shows images of lung tissues of the animal models in Groups 1-4 on day 20 after induction of lung metastasis.

As shown in FIGS. 7A and 7B, no tumors were found in the lungs of Group 4 administered the self-assembled nanoparticles (LT-NPs) and PD-L1 Ab and irradiated with visible light and large numbers of tumors were found in the lungs of Groups 1, 2, and 3. In conclusion, the co-administration of the self-assembled nanoparticles (LT-NPs) and PD-L1 Ab and irradiation with visible light are effective in preventing and treating cancer metastasis.

Figure 7C:
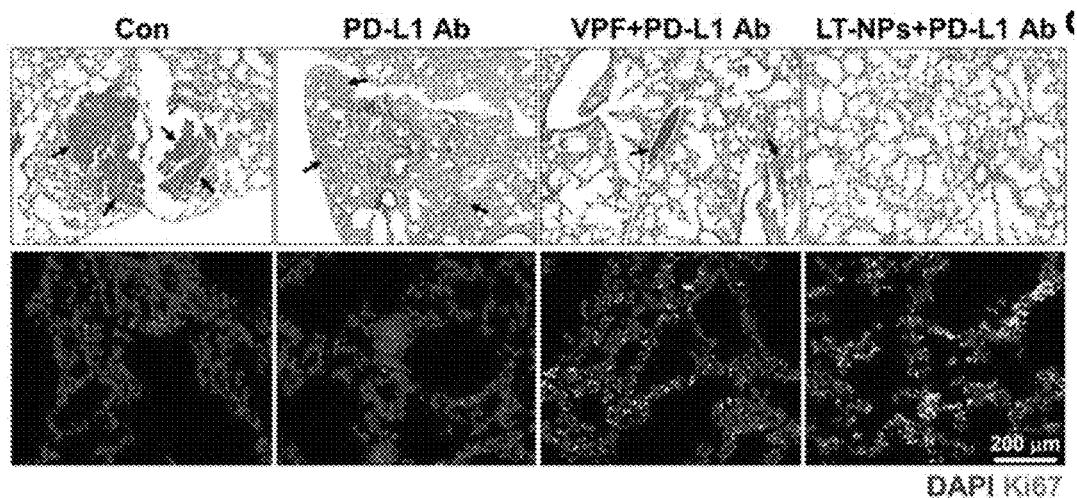
FIG. 7C shows the results of H&E staining and immunohistological staining (Ki67) for lung tissues excised from animal models in Groups 1-4 on day 20 after induction of lung metastasis.
Figure 7D:
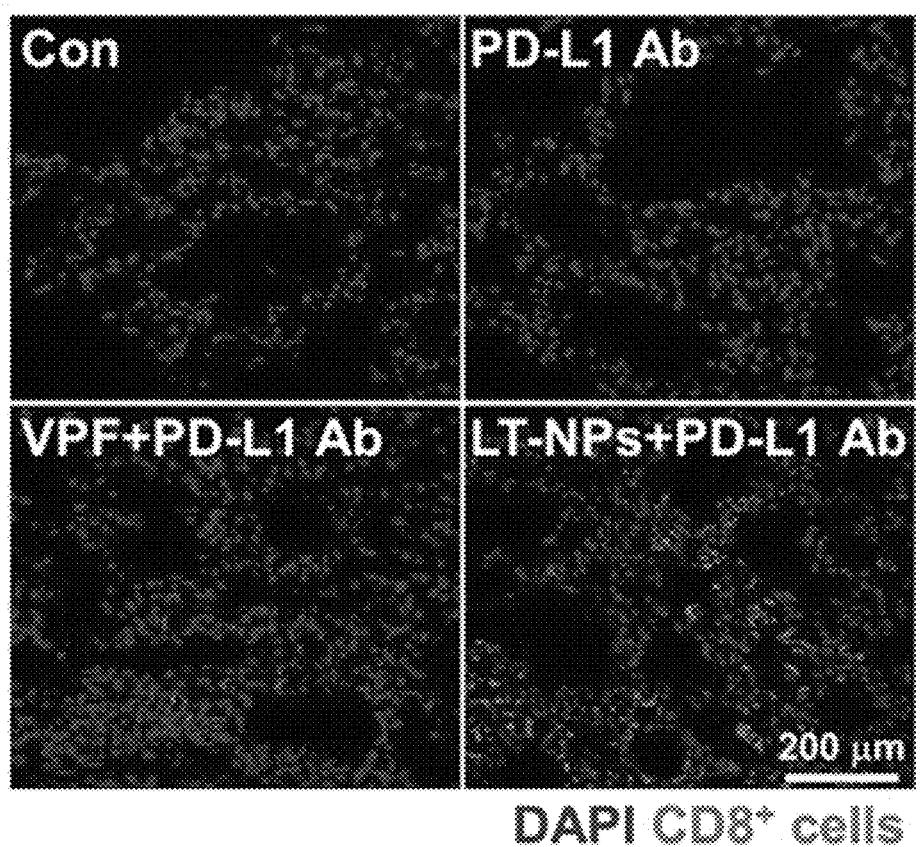
FIG. 7D shows the results of H&E staining and immunohistological staining (Ki67) for metastatic cancer tissues in animal models in Groups 1-4 on day 20 after induction of lung metastasis to determine the degrees of infiltration of cytotoxic T cells into the metastatic cancer tissues.

FIG. 7C shows the results of H&E staining and immunohistological staining for lung tissues excised from animal models in Groups 1-4 on day 20 after induction of lung metastasis and FIG. 7D shows the results of H&E staining and immunohistological staining for metastatic cancer tissues in animal models in Groups 1-4 on day 20 after induction of lung metastasis to determine the degrees of infiltration of immune cells into the metastatic cancer tissues.

As shown in FIGS. 7C and 7D, the number of cytotoxic T cells (CD8+ T cells) infiltrated into the lung tissues of Group 4 administered the self-assembled nanoparticles (LT-NPs) and PD-L1 Ab and irradiated with visible light was significantly larger than those of the other groups. In conclusion, the self-assembled nanoparticles (LT-NPs) induce potent immunogenicity in vivo.

Figure 7E:
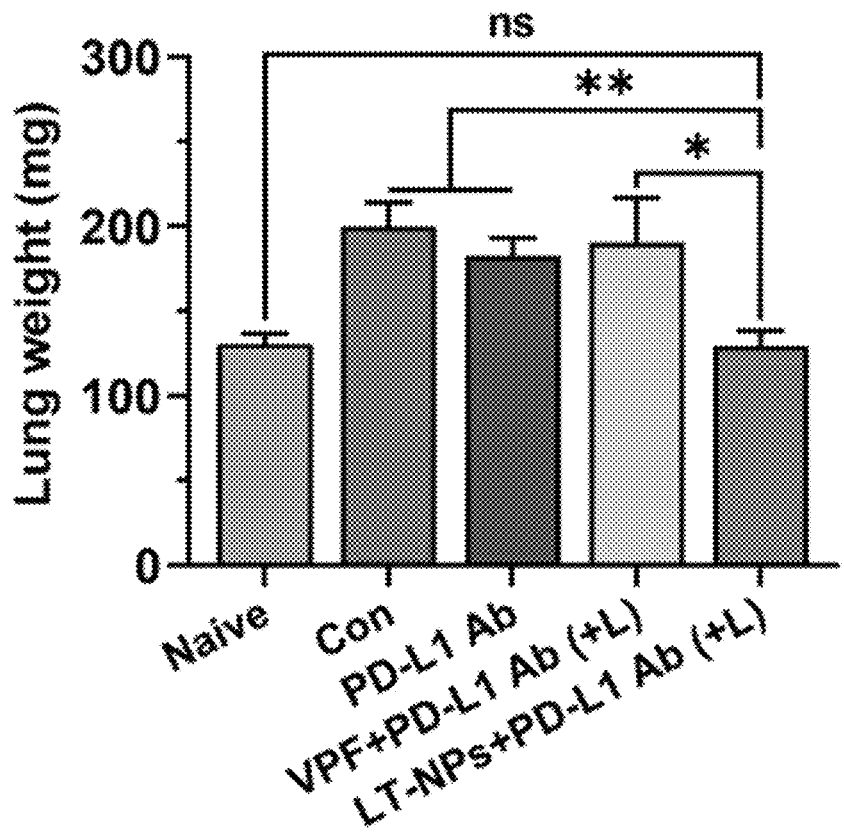
FIG. 7E shows the weights of lung tissues of animal models in Groups 1-4 on day 20 after induction of lung metastasis.

FIG. 7E shows the weights of lung tissues of the animal models in Groups 1-4 on day 20 after induction of lung metastasis. As shown in FIG. 7E, no significant difference was observed between Group 4 administered the self-assembled nanoparticles (LT-NPs) and PD-L1 Ab and irradiated with visible light and the normal group (Naive). In contrast, the lung weights were significantly increased in Groups 1, 2, and 3.

In conclusion, the self-assembled nanoparticles (LT-NPs) do not cause a change in lung weight due to their ability to completely block cancer metastasis, unlike the conventional anticancer drug.

Figure 7F:
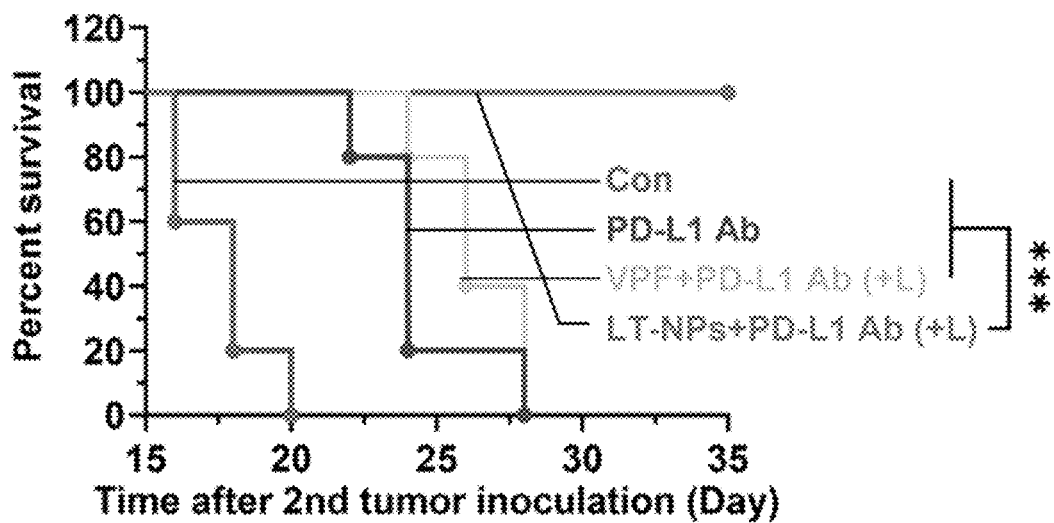
FIG. 7F shows the survival rates (%) of animal models in Groups 1-4 on day 20 after induction of lung metastasis.

FIG. 7F shows the survival rates (%) of the animal models in Groups 1-4 on day 20 after induction of lung metastasis. As shown in FIG. 7F, the survival rate (%) of the animal models in Group 4 administered the self-assembled nanoparticles (LT-NPs) and PD-L1 Ab and irradiated with visible light was significantly increased compared to those in the other groups. Specifically, the survival rate (%) was maintained at 100% in Group 4 administered the self-assembled nanoparticles (LT-NPs) and PD-L1 Ab and irradiated with visible light, whereas all animal models in untreated Group 1 died within day 20 and all animal models in Groups 2 and 3 administered the conventional anticancer drug in combination with the immune checkpoint inhibitor died in a period shorter than 30 days.

In conclusion, unlike the conventional anticancer drug, the self-assembled nanoparticles (LT-NPs) induce not only apoptosis in cancer cells but also potent immunogenicity in vivo to cure cancer and effectively prevent cancer recurrence and metastasis, achieving a survival rate of 100%.

What is claimed is:

1. Self-assembled nanoparticles comprising complexes in which a hydrophobic anticancer drug and a photosensitizer are bonded to one end and the other end of a central amphipathic peptide represented by Formula 1, respectively:

(SEQ ID NO: 2)
Xaa1-Arg-Arg-Gly (1)

wherein Xaa is selected from alanine, valine, isoleucine, leucine, methionine, phenylalanine, tyrosine, and tryptophan.

2. The self-assembled nanoparticles according to claim 1, wherein the self-assembled nanoparticles have an average diameter of 50 to 500 nm.

3. The self-assembled nanoparticles according to claim 1, wherein the hydrophobic anticancer drug is selected from the group consisting of doxorubicin, cyclophosphamide, mechlorethamine, uramustine, melphalan, chlorambucil, ifosfamide, bendamustine, carmustine, lomustine, streptozocin, busulfan, dacarbazine, temozolomide, thiotepa, altretamine, duocarmycin, cisplatin, carboplatin, nedaplatin, oxaliplatin, satraplatin, triplatin tetranitrate, 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, camptothecin, topotecan, irinotecan, etoposide, teniposide, mitoxantrone, paclitaxel, docetaxel, ixabepilone, vinblastine, vincristine, vindesine, vinorelbine, estramustine, maytansine, mertansine (DM1), DM4, dolastatin, auristatin E, auristatin F, monomethyl auristatin E, monomethyl auristatin F, and combinations thereof.

4. The self-assembled nanoparticles according to claim 1, wherein the photosensitizer is selected from protoporphyrin

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Amphipathic peptide

<400> SEQUENCE: 1

Phe Arg Arg Gly
1

<210> SEQ ID NO 2
<211> LENGTH: 4
<212> TYPE: PRT
<213> ORGANISM: Artificial Sequence
<220> FEATURE:
<223> OTHER INFORMATION: Amphipathic peptide
<220> FEATURE:
<221> NAME/KEY: MISC_FEATURE
<222> LOCATION: (1)..(1)
<223> OTHER INFORMATION: Xaa is selected from alanine, valine,
      isoleucine, leucine, methionine, phenylalanine, tyrosine, and
      tryptophan

<400> SEQUENCE: 2

Xaa Arg Arg Gly
1

IX, verteporfin, Foscan, Levulan, Metvix, Hexvix, Purlytin, Photochlor, Lutex, Talaporfin, and mixtures thereof.

5. A pharmaceutical composition for treating cancer comprising the self-assembled nanoparticles according to claim 1 as active ingredients.

6. The pharmaceutical composition according to claim 5, wherein the cancer is selected from the group consisting of brain tumor, benign astrocytoma, malignant astrocytoma, pituitary adenoma, meningioma, central nervous system lymphoma, oligodendroglioma, craniopharyngioma, ependymoma, brain stem tumor, head and neck tumor, laryngeal cancer, oropharyngeal cancer, nasal cavity/paranasal sinus cancer, nasopharyngeal cancer, salivary gland cancer, hypopharyngeal cancer, thyroid cancer, oral cavity cancer, chest tumor, small cell lung cancer, non-small cell lung cancer, thymus cancer, mediastinal tumor, esophageal cancer, breast cancer, male breast cancer, abdominal tumor, stomach cancer, liver cancer, gall bladder cancer, biliary tract cancer, pancreatic cancer, small intestine cancer, large intestine cancer, anal cancer, bladder cancer, kidney cancer, prostate cancer, testicular cancer, uterine cancer, cervical cancer, endometrial cancer, ovarian cancer, uterine sarcoma, squamous cell carcinoma, skin cancer, resistant cancers, recurrent cancers, metastatic cancers, and combinations thereof.

7. The pharmaceutical composition according to claim 5, further comprising an immune checkpoint inhibitor.

* * * * *